(12) United States Patent
Sandell et al.

(10) Patent No.: US 6,419,827 B1
(45) Date of Patent: Jul. 16, 2002

(54) PURIFICATION APPARATUS AND METHOD

(75) Inventors: Donald R. Sandell, San Jose; Kevin S. Bodner; Mark Borodkin, both of San Mateo; Mark Oldham, Los Gatos; Jon Hoshizaki, Cupertino, all of CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/552,301

(22) Filed: Apr. 18, 2000

Related U.S. Application Data

(63) Continuation-in-part of application No. 09/182,946, filed on Oct. 29, 1998, now Pat. No. 6,159,368.

(51) Int. Cl.[7] .............................................. B01D 63/00
(52) U.S. Cl. ............................. 210/321.75; 210/416.1; 422/101; 422/104; 422/239; 422/298
(58) Field of Search ........................... 210/321.75, 767, 210/416.1; 422/101, 104, 239, 258; 435/297.1

(56) References Cited

U.S. PATENT DOCUMENTS

| | | |
|---|---|---|
| 3,463,322 A | 8/1969 | Gerarde |
| 3,721,364 A | 3/1973 | Lukaschewitz et al. |
| 4,167,875 A | 9/1979 | Meakin |

(List continued on next page.)

FOREIGN PATENT DOCUMENTS

| | | |
|---|---|---|
| DE | 4022792 | 2/1992 |
| DE | 297 22 473 U1 | 2/1998 |
| DE | 297 22 473 U1 | 4/1998 |
| DE | 196 52 327 A1 | 6/1998 |
| EP | 0 131 934 B1 | 1/1985 |
| EP | 0 359 249 A2 | 3/1990 |
| EP | 0 502 371 B1 | 9/1992 |
| EP | 0 645 187 A2 | 3/1995 |
| EP | 676643 A2 | 6/1995 |
| EP | 0 903 176 A2 | 3/1999 |
| EP | 0 925 828 A1 | 6/1999 |
| GB | 2 246 081 A | 1/1992 |
| WO | 86/07606 | 12/1986 |
| WO | 94/28111 | 12/1994 |
| WO | 95/30139 | 11/1995 |
| WO | 98/10853 | 3/1998 |
| WO | WO 00/25922 | 5/2000 |

OTHER PUBLICATIONS

"mRNA Isolation Using Event", BIONEWS. 01:3 (1996).
"Multiscreen Assay System," Multiscreen Assay System, Rev. C, Updated: Apr. 13, 1998. Publication P17479 Revision C. Internet address: http//millispider.millipore.com/analytical/manuals/p17479a.htm 1–4.
Newell, J.A. and Horton, H.L. (eds.), "Overload, Tripping, and Stop Mechanisms," Ingenious Mechanisms. Industrial Press Inc., New York. 109–111 (1967).
QIAGEN Product Guide. 16, 37–38 (1997).

(List continued on next page.)

*Primary Examiner*—Ana Fortuna
(74) *Attorney, Agent, or Firm*—Kilyk & Bowersox, P.L.L.C.

(57) ABSTRACT

The invention includes a filtration apparatus for processing a plurality of fluid samples into sample wells is provided. In one embodiment, the filtration apparatus includes a purification tray and a sample well tray with a plurality of sample wells. The purification tray includes a filter plate having a plurality of columns with discharge openings at the bottom thereof, at least one filter positioned in the columns of the filter plate for filtering the fluid samples as they pass therethrough, a heat plate positioned adjacent the columns of the filter plate, and a vent plate positioned below the heat plate. The heat plate is configured for transferring heat to the columns of the filter plate. The vent plate includes vents for permitting aerosols from the sample wells of the sample well tray to escape. A sample well tray with a plurality of the sample wells is positioned so that the sample wells align with the discharge openings of the filter plate columns to receive the liquid sample therein.

41 Claims, 24 Drawing Sheets

U.S. PATENT DOCUMENTS

| | | |
|---|---|---|
| 4,246,339 A | 1/1981 | Cole et al. |
| 4,304,865 A | 12/1981 | O'Brien et al. |
| 4,734,192 A | 3/1988 | Champion et al. |
| 4,927,604 A | 5/1990 | Mathus et al. |
| 4,948,442 A | 8/1990 | Manns |
| 4,948,564 A | 8/1990 | Root et al. |
| 4,969,306 A | 11/1990 | Wallin |
| 5,002,889 A | 3/1991 | Klein |
| 5,047,215 A | 9/1991 | Manns |
| 5,108,704 A | 4/1992 | Bowers et al. |
| 5,110,556 A | 5/1992 | Lyman et al. |
| 5,114,681 A | 5/1992 | Bertoncini et al. |
| 5,116,496 A | 5/1992 | Scott |
| 5,141,719 A | 8/1992 | Fernwood et al. |
| 5,201,348 A | 4/1993 | Lurz |
| 5,208,161 A | 5/1993 | Saunders et al. |
| 5,227,137 A | 7/1993 | Monti et al. |
| 5,264,184 A | 11/1993 | Aysta et al. |
| 5,282,543 A | 2/1994 | Picozza et al. |
| 5,342,581 A | 8/1994 | Sanadi |
| 5,352,086 A | 10/1994 | Mank |
| 5,368,729 A | 11/1994 | Stefkovich et al. |
| 5,380,437 A | 1/1995 | Bertoncini |
| 5,401,637 A | 3/1995 | Pocock |
| 5,409,832 A | 4/1995 | Pocock |
| 5,459,300 A | 10/1995 | Kasman |
| 5,464,541 A | 11/1995 | Aysta et al. |
| 5,516,490 A | 5/1996 | Sanadi |
| 5,604,130 A | 2/1997 | Warner et al. |
| 5,620,663 A | 4/1997 | Aysta et al. |
| 5,650,323 A | 7/1997 | Root |
| 5,665,247 A | 9/1997 | Valus et al. |
| 5,679,310 A | 10/1997 | Manns |
| 5,681,492 A | 10/1997 | Van Praet |
| 5,721,136 A | 2/1998 | Finney et al. |
| 5,736,105 A | 4/1998 | Astle |
| 5,736,106 A | 4/1998 | Ishiguro et al. |
| 5,741,463 A | 4/1998 | Sanadi |
| 5,792,430 A | 8/1998 | Hamper ..................... 422/131 |
| 6,159,368 A | * 12/2000 | Moring et al. ......... 210/321.75 |

OTHER PUBLICATIONS

Ruppert, A. et al., "A Filtration Method for Plasmid Isolation Using Microtiter Filter Plates," Analytical Biochemistry. 230: 130–134 (1995).

"Technical Data on Ultra–Pure QM–A Quartz Filters," Whatman. Publication No. 860 QM–AA (1992).

"Genesis Robotic Microplate Processor," TECAN. Document No. 390981, pp. 1–8, Ver. Nov. 1997.

"The Genesis Series of RSPs," TECAN. Document No. 390696, pp. 1–8, Ver. Oct. 1997.

"Whatman Ultra–Pure QM–A Quartz Filters," Whatman. Data Sheet No. 860 QM–AA (1992).

European Search Report, Mar. 2000, EPO.

* cited by examiner

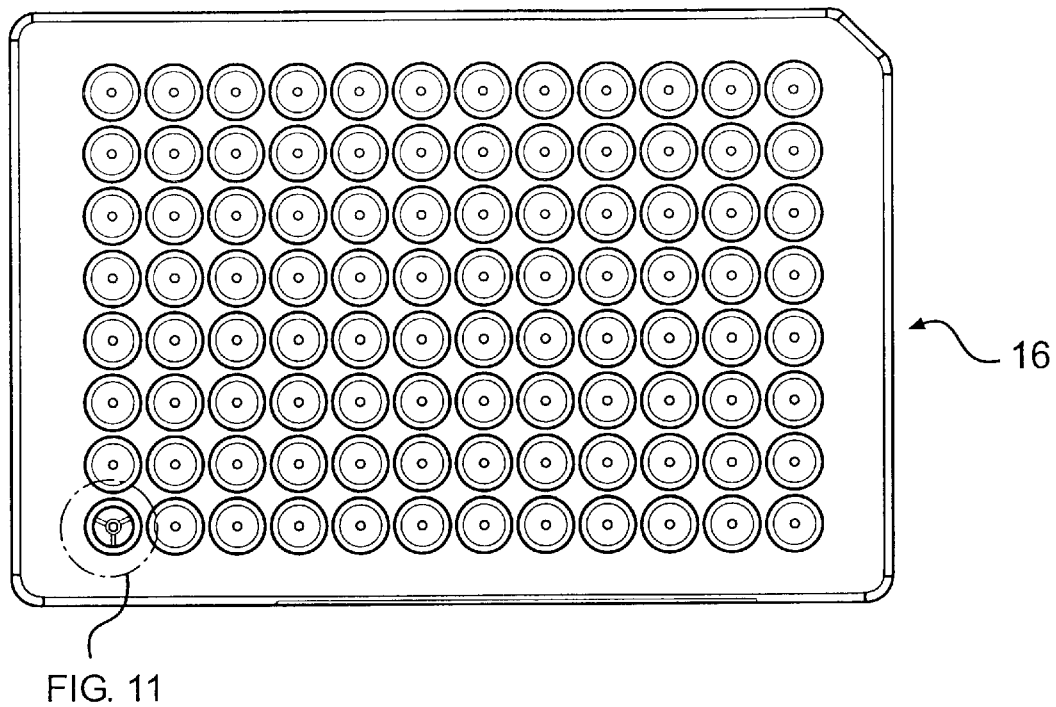
FIG. 11
FIG. 9
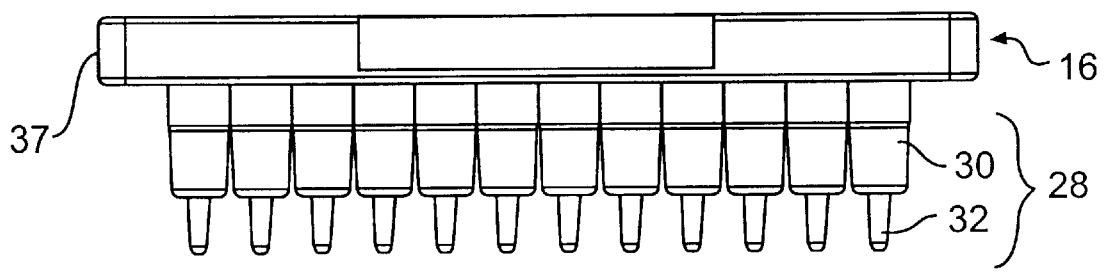
FIG. 10

PURIFICATION APPARATUS AND METHOD

This application is a Continuation-In-Part of Application Ser. No. 09/182,946, filed Oct. 29, 1998, now U.S. Pat. No. 6,159,368 the contents of which are hereby incorporated by reference herein.

BACKGROUND OF THE INVENTION

1. Field of the Invention

The present invention relates in one aspect to a purification apparatus and method for processing a plurality of fluid samples of biological material. In a particular embodiment, this invention relates to a purification apparatus for filtering fluid samples through filters of a purification tray into the sample wells of a sample well tray in a manner that minimizes the risk of cross-contamination between adjacent sample wells.

2. Description of the Related Art

Biological testing using sample trays with a plurality of sample wells has become increasingly popular in recent years. Biological testing of samples in an array of wells is utilized in a wide variety of applications such as genome sequencing, drug discovery, and disease detection and monitoring. In typical applications, it is desirable to process the biological sample through a filter prior to placing the biological sample in the sample wells. A purification tray is typically provided for processing the biological samples.

For example, in one particular process used to prepare RNA, a biological sample which has undergone sample preparation steps is placed in the columns of a purification tray. A series of washes are performed to remove any remaining DNA and cellular debris from the filter elements that may inhibit the later reaction. As a result, RNA is trapped on filter material located in the columns. Next, with a sample well tray positioned immediately below the purification tray, an elution solution is dropped into the columns so that the purified RNA solubilizes and leaves the filter to be discharged into the sample wells of the sample well tray. The sample well trays with the purified RNA may then undergo any suitable thermal or chemical operation.

During the process of discharging the biological sample into the sample wells, aerosols are typically created in and above the sample wells. In a typical system for processing a biological sample, a purification tray is placed immediately on top of the well tray. During the process of drawing the solution through the filters and into the sample wells, aerosols are typically formed in the sample wells and in the region between the sample well tray and the purification tray. Existing devices are inadequate in removing the aerosols from the sample wells without cross-contamination occurring between adjacent sample wells. This type of cross-contamination adversely affects the accuracy and effectiveness of the later operations.

It is desirable to provide a purification apparatus for processing a plurality of fluid samples that reduces the amount of cross-contamination between wells. In addition, it is particularly desirable to provide such an apparatus that is suitable for use at higher temperatures.

SUMMARY OF THE INVENTION

The advantages and purposes of the invention will be set forth in part in the description which follows, and in part will be apparent from the description, or may be appreciated by practice of the invention. The advantages and purposes of the invention will be realized and attained by means of the elements and combinations particularly pointed out in the appended claims.

In one aspect, the invention includes a filtration apparatus for processing a plurality of fluid samples. The filtration apparatus includes a purification tray and a sample well tray. The purification tray includes a filter plate, a plurality of filters and a plate including flow obstructions. The filter plate has a plurality of columns with a discharge opening at the bottom of each column. The plurality of filters align with the columns of the filter plate. The sample well tray has a plurality of sample wells aligned with the columns of the filter plate for receiving fluid from the discharge openings. The vent plate is positioned in a space between the filter plate and the sample well tray. The vent plate flow obstructions are positioned adjacent the sample wells in order to limit cross-contamination between sample wells. The flow obstructions define at least one discrete flow path for permitting aerosols from a sample well to pass therethrough out of the respective sample well while preventing the aerosols from contaminating adjacent sample wells. In one embodiment, the purification tray further includes a heat transfer plate positioned between at least a portion of the filter plate and at least a portion of the vent plate. In another embodiment, the sample well tray includes a removal mechanism for assisting in the removal of the sample well tray.

In another aspect, the invention includes a purification tray for processing a plurality of fluid samples into sample wells. The purification tray includes a filter plate having a plurality of columns with discharge openings at the bottom thereof, at least one filter positioned in the columns of the filter plate for filtering the fluid samples as they pass therethrough, a vent plate positioned between the filter plate and the sample wells, and a heat transfer plate. The vent plate includes vents for permitting aerosols from the sample wells to escape, while preventing the aerosols from contaminating sample wells. The heat transfer plate is positioned between the vent plate and a portion of the filter plate and is configured to transfer heat to the fluids in the columns of the filter plate. In a further aspect of the invention, the invention includes a filling apparatus for filling sample wells with a liquid sample. The filling apparatus includes a filling plate, a heat transfer plate, an aerosol guard, and a sample tray. The filling plate has a plurality of filling columns having discharge openings adjacent the bottom thereof through which a liquid sample may exit the filling column to flow into a sample well. The heat transfer plate transfers heat to the filling columns of the filling plate and is in contact with the filling plate. The aerosol guard is attached to a surface of the heat transfer plate, and includes a plate with a plurality of passages for the flow of aerosols therethrough. The sample tray includes a plurality of sample wells for receiving liquid sample from at least one of the discharge openings of the filling plate and is positioned with respect to the aerosol guard to permit aerosols in the sample wells to exit from the sample wells through apertures in the aerosol guard.

In a yet further aspect of the invention, the invention includes an aerosol guard for directing aerosols formed in sample wells away from the sample wells. The aerosol guard includes a plate of substantially non-porous material and a plurality of raised surfaces on a first side of the plate. The raised surfaces direct aerosols from sample wells to flow through the aerosol guard. The raised surfaces are positioned around corresponding sample wells to inhibit cross-contamination between sample wells.

In another aspect, the present invention is directed toward a method of filtering liquid samples into sample wells in a sample well tray using a purification tray. The method includes providing a purification tray and sample well tray. The purification tray has a plurality of columns with discharge openings at the bottom thereof. The method further includes providing filters in the plurality of columns, introducing a liquid sample into at least one column of the purification tray so that the liquid sample contacts the filter in the column, applying a pressure differential to the column so that the liquid sample is urged through the filter and out of a discharge opening of the column into the sample well, and obstructing aerosols formed in the sample wells from mixing with the liquid sample of an adjacent sample well by providing an aerosol guard with a discrete flow path out of the sample well.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

FIG. 9 is a top view of the purification tray of FIG. 1 with one column having the filter removed therefrom;

FIG. 10 is a front view of the purification tray of FIG. 9;

Figure 1:
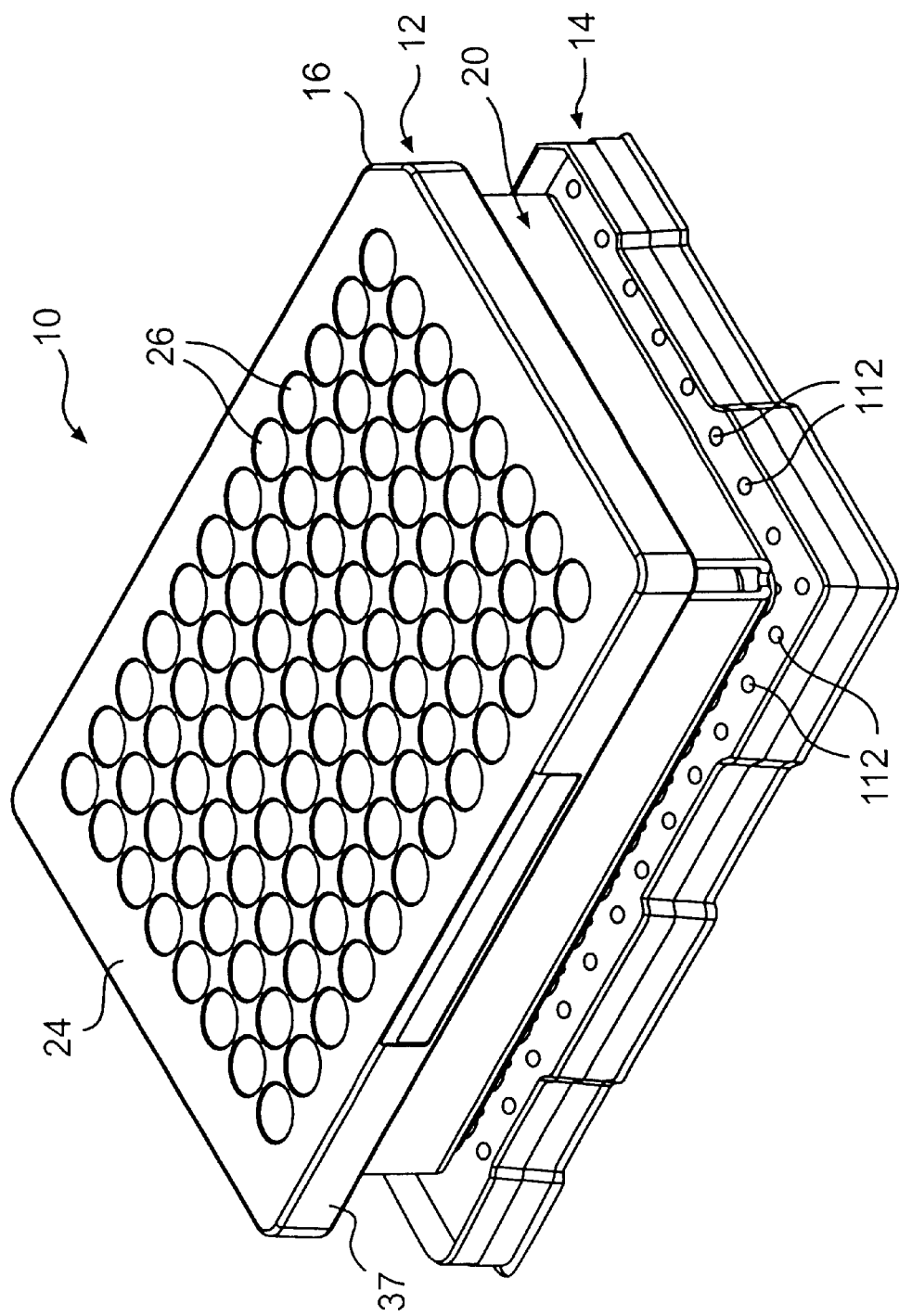
FIG. 1 is a perspective view of a purification apparatus having a purification tray and sample well tray according to the invention.
Figure 2:
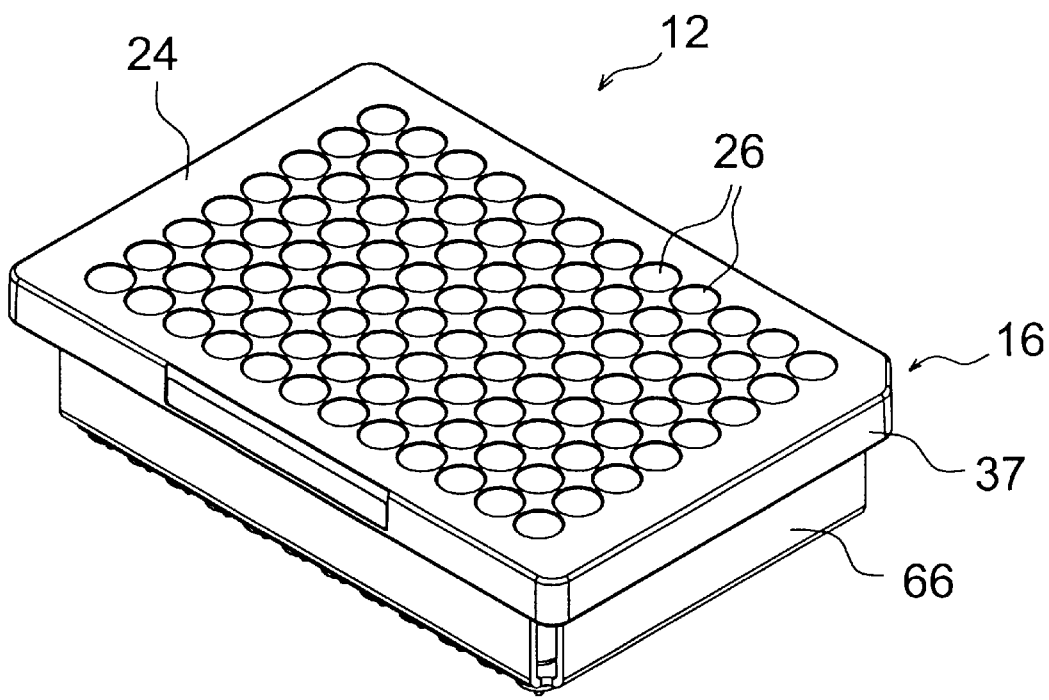
FIG. 2 is a perspective view of the purification tray of FIG. 1.
Figure 3:
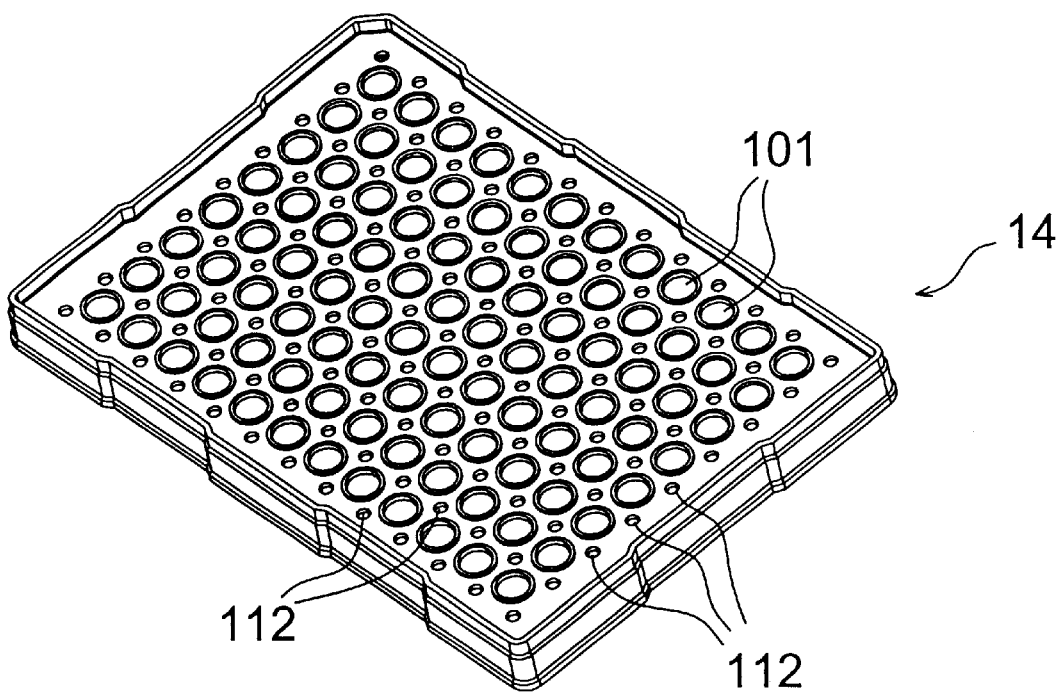
FIG. 3 is a perspective view of the sample well tray of FIG. 1

FIG. 18 is a top view of the sample well tray of FIG. 1;

FIG. 19 is a section view along line XIX—XIX of FIG. 18;

FIG. 20 is a perspective view of a carriage for the purification apparatus of FIG. 1 in an unassembled state:

FIG. 21 is a bottom perspective view of a purification tray according to a second embodiment of the present invention;

FIG. 22 is a close-up bottom perspective view of the purification tray of FIG. 21;

FIG. 23 is a perspective view of the purification tray of FIG. 21 with an aerosol guard in an unassembled state;

FIG. 24 is a perspective view of the sample well tray for use with the purification tray of FIG. 21;

FIG. 25 is a schematic illustrating the alignment of the purification tray and sample well tray of the second embodiment;

FIG. 26A is a cross-section of stacked conventional sample well trays;

FIG. 26B is a cross-section of stacked sample well trays according to the present invention:

FIG. 27 is a perspective view of an alternate sample well tray having a removal mechanism;

FIGS. 28A and 28B are section views of the removal mechanism for the sample well tray of FIG. 27 in a disengaged and engaged position, respectively;

FIG. 29 is a perspective view of another alternate sample well tray having a removal mechanism; and FIGS. 30A and 30B are section views of the removal mechanism for the sample well tray of FIG. 29 in a disengaged and engaged position, respectively.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

In accordance with the present invention, a purification apparatus for processing a plurality of fluid samples into sample wells is provided. In one embodiment of the present invention, the purification apparatus includes a purification tray and a sample well tray with a plurality of sample wells. The purification tray includes a filter plate having a plurality of columns with discharge openings at the bottom thereof, at least one filter positioned in the columns of the filter plate for filtering the fluid samples as they pass therethrough, a heat plate positioned adjacent the columns of the filter plate, and a vent plate positioned below the heat plate. The heat plate is configured for providing heat to the liquid in the columns of the filter plate. The vent plate includes vents for permitting aerosols from the sample wells of the sample well tray to escape while preventing the aerosols from contaminating adjacent sample wells. A sample well tray with a plurality of the sample wells is positioned so that the sample wells align with the discharge openings of the filter plate columns to receive the liquid sample therein.

As embodied herein and shown in the first embodiment of FIGS. 1–20, the purification apparatus 10 for processing a plurality of fluid samples includes a purification tray 12 and sample well tray 14. The purification tray 12 includes a filter plate 16, a plurality of filters 18, a heat plate 20, and a vent plate 22.

The purification apparatus of the present invention may be used for filtering fluid samples, such as biological materials, into a plurality of sample wells of a sample well tray. The specific procedure for filtering the fluid samples may be any known procedure. For purposes of example only, the procedure which will be primarily discussed below is the purification of nucleic acids such as RNA for PCR analyses, although the purification apparatus of the present invention may be used with any known filtering process used with purification trays. Other processes besides RNA purification include, for example, the purification of DNA, the extraction and purification of RNA or DNA from blood, and the extraction and purification of proteins. Other filtrations processes are suitable with the present invention. The apparatus of the present invention is also suited for purifying specific sequences of DNA and RNA by varying the filter element of the purification tray.

Prior to undergoing a typical filtering procedure, a biological material such as a nucleic acid is captured or immobilized on a filter in a column of a purification tray. The biological material, after undergoing a series of washes or other steps, is then solubilized and drawn through the filter into an aligned sample well positioned below the filter during an elution step. The biological material is said to be purified by the procedure. The biological material is thereby positioned in the sample well of the sample well tray. The sample well tray is then typically removed from the apparatus and the purification process can be repeated again for a different sample well tray. The removed sample well tray can then be stored for a period of time, or alternatively, immediately used for a chemical or thermal operation such as thermal cycling for PCR reactions.

The apparatus of the present invention is also suited for filtering processes that require heating during the filtration of the biological samples. The purification tray is designed to include a heat transfer plate that may be connected to a heat source as will be described in greater detail below. The ability to heat the purification tray allows the purification apparatus to be used for a wider range of processes. The present invention is also suitable in procedures where the apparatus does not undergo temperature fluctuations during the filtering process.

The purification tray of the present invention is suitable for use in workstations for sample preparations. For example, the purification tray and sample well tray of the present invention are suited for use in the ABI PRISM 6700 Automated Nucleic Acid Workstation manufactured by PE Biosystems. The purification tray and sample well tray are also suitable for use with a wide variety of other sample preparation workstations.

In accordance with the present invention, the purification tray includes a filter plate having a plurality of columns with discharge openings at the bottom thereof. As embodied herein and shown in FIGS. 1–20, the filter plate 16 includes a top plate portion 24 with a plurality of cylindrical openings 26. Although the embodiment of FIGS. 1–20 shows the filter plate having ninety-six openings, the present invention is suitable with any of the other common configurations, such as 384, 60, or other numbers. The filter plate (and corresponding sample well tray) of the present invention is also suitable with other configurations having any number of openings ranging from one to several thousand. The number of openings in the filter plate 16 Will typically match the number of sample wells in the sample well tray. The openings in the filter plate are typically arranged in a rectangular array, such as the 8 by 12 array best shown in FIG. 5. The filter plate of the purification tray is compatible with a wide range of standard format sample well trays and is also compatible with existing robotic handling devices. However, the filter plate could alternately be arranged to be compatible with nonstandard configurations, such as non-rectangular formats.

Figure 4:
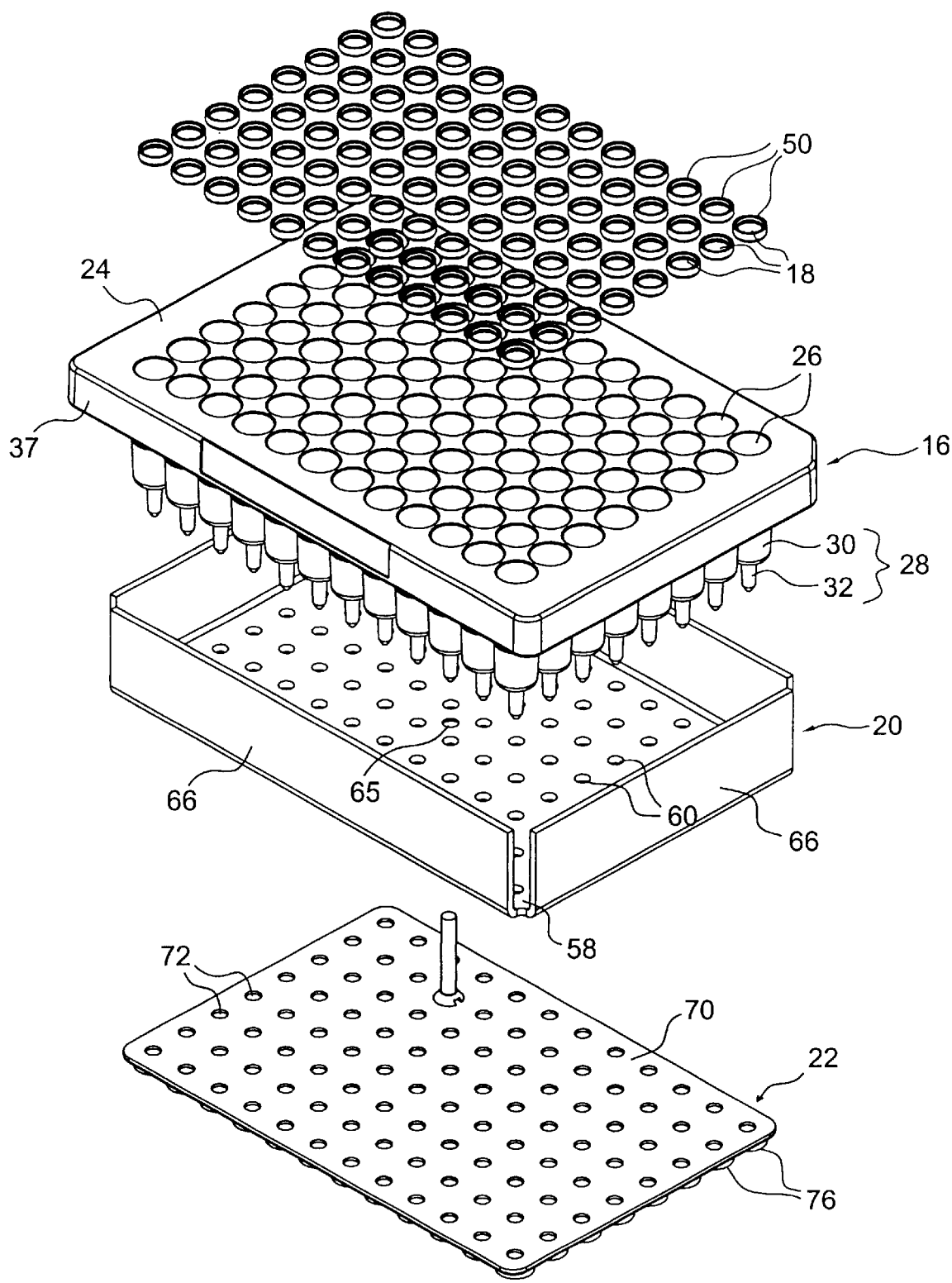
FIG. 4 is a perspective view of the purification tray of FIG. 1 in an unassembled state.
Figure 5:
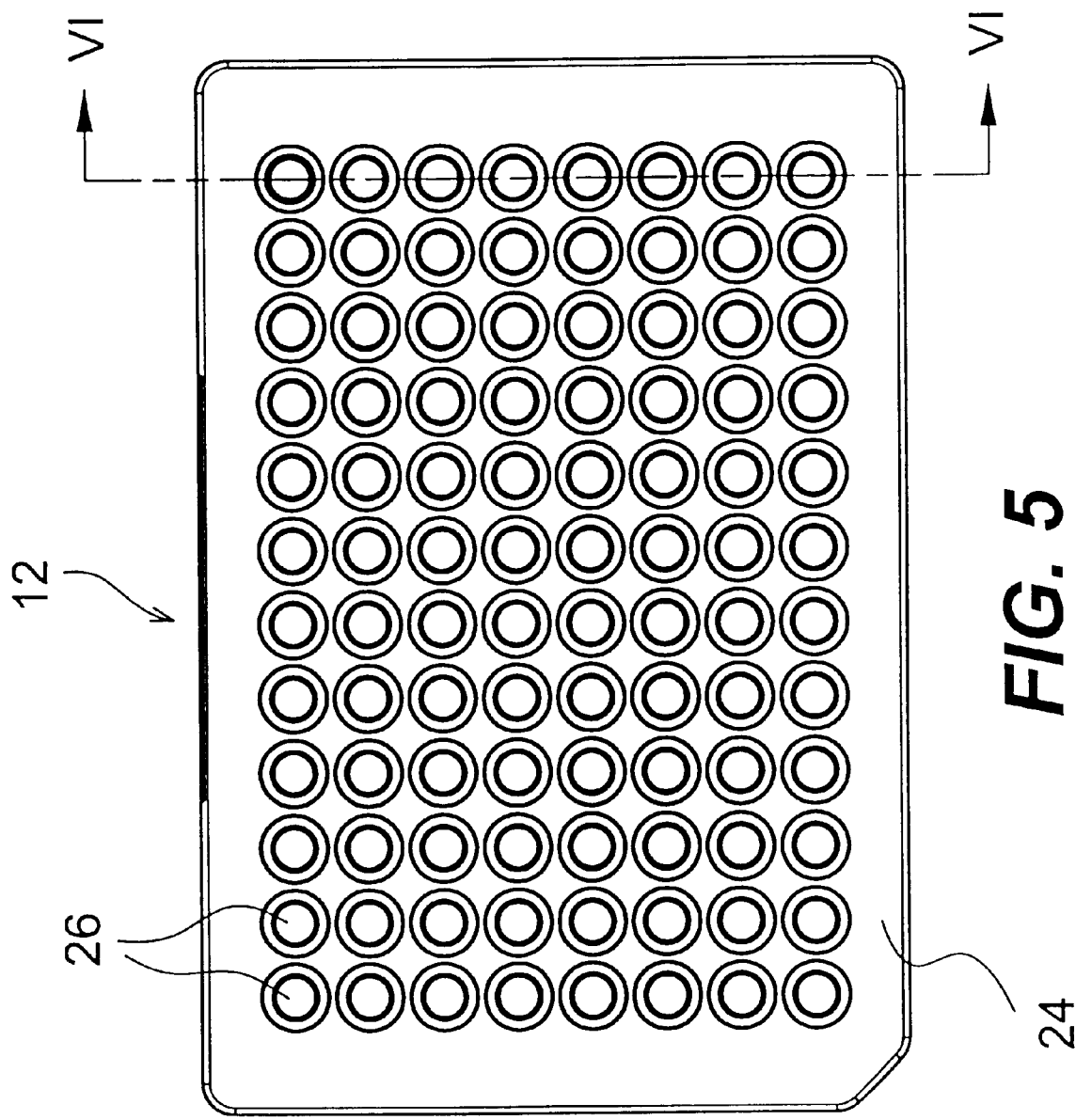
FIG. 5 is a top view of the purification tray of FIG. 1 with filters inserted in columns of the purification tray.
Figure 6:
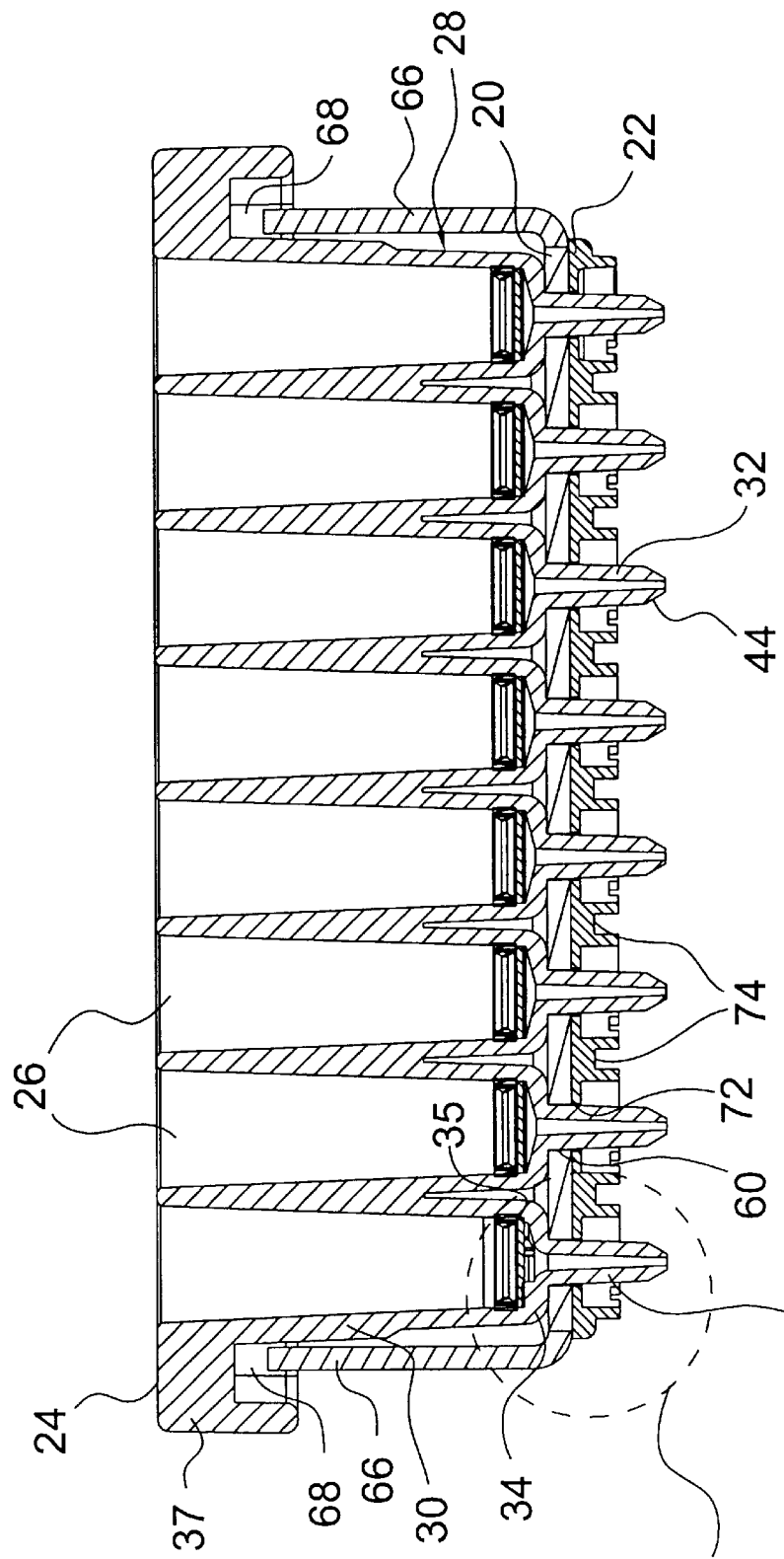
FIG. 6 is a section view of the purification tray along line VI—VI of FIG. 5.

The filter plate 16 includes a plurality of columns 28 extending downward from the top plate portion 24 of the filter plate, as best shown in FIGS. 4, 6, and 10. The columns 28 define a first tapered cylindrical portion 30 and a second tapered cylindrical portion or drip director 32. The first tapered cylindrical portion 30 is shown, for example in FIG. 6, as being slightly tapered so that the inside diameter of the first tapered cylindrical portion 30 decreases as the column extends further from the top plate portion 24 of the filter plate. The filter plate openings 26 have a larger diameter at the portion than at the portion where the filter elements are located as best shown in FIG. 6. The slightly-tapered configuration enhances the flow of the fluid sample through the first tapered cylindrical portion. The taper also enables the filters to be more easily inserted in the columns. The taper is also a result of the injection-molding process by which the filter plate is typically made. Alternately, the first tapered cylindrical portion of the column may be completely cylindrical, with a constant diameter throughout its length. Although the Figures show the columns 28 as being substantially circular in horizontal cross section, it should be appreciated that the columns may of any desired geometrical cross-section such as oval, square, rectangular, triangular, etc.

In the preferred embodiment shown in the Figures, the columns are made out of substantially unitary construction. Because the columns are made out of substantially unitary construction, the likelihood of leaking is minimized, especially at high temperatures. Alternately, each column could be made out of several members, however, the likelihood of leaking is typically increased by such a construction.

Figure 7:
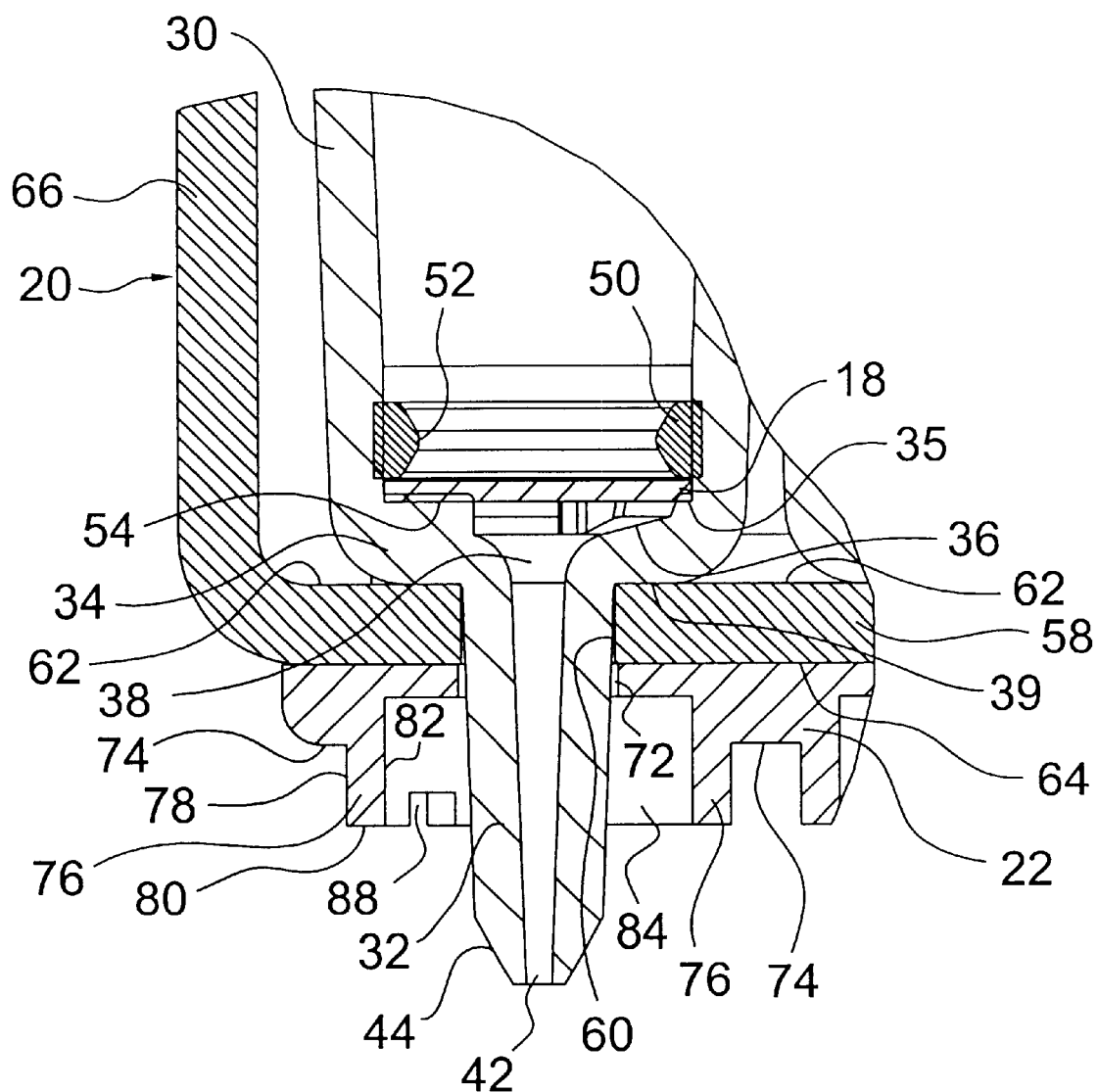
FIG. 7 is a close-up section view of the purification tray of section VII of FIG. 6.

As best shown in FIGS. 6 and 7, the end of the first tapered cylindrical portion 30 farthest from the top plate portion 24 leads to an annular connecting portion 34. The annular connecting portion 34 connects the first tapered cylindrical portion 30 and the second tapered cylindrical portion or drip director 32. The annular connecting portion 34 is a circular rim that projects perpendicular to the walls of the first tapered cylindrical portion 30. The annular connecting portion 34 defines the bottom of the first tapered portion 30. The annular connecting portion 34 includes a flat outer annular surface 35 and a tapered floor portion 36, as best shown in FIG. 7. The flat outer annular surface 35 serves as a stop on which the filter 18 is positioned, as will be described in greater detail below.

Figure 8:
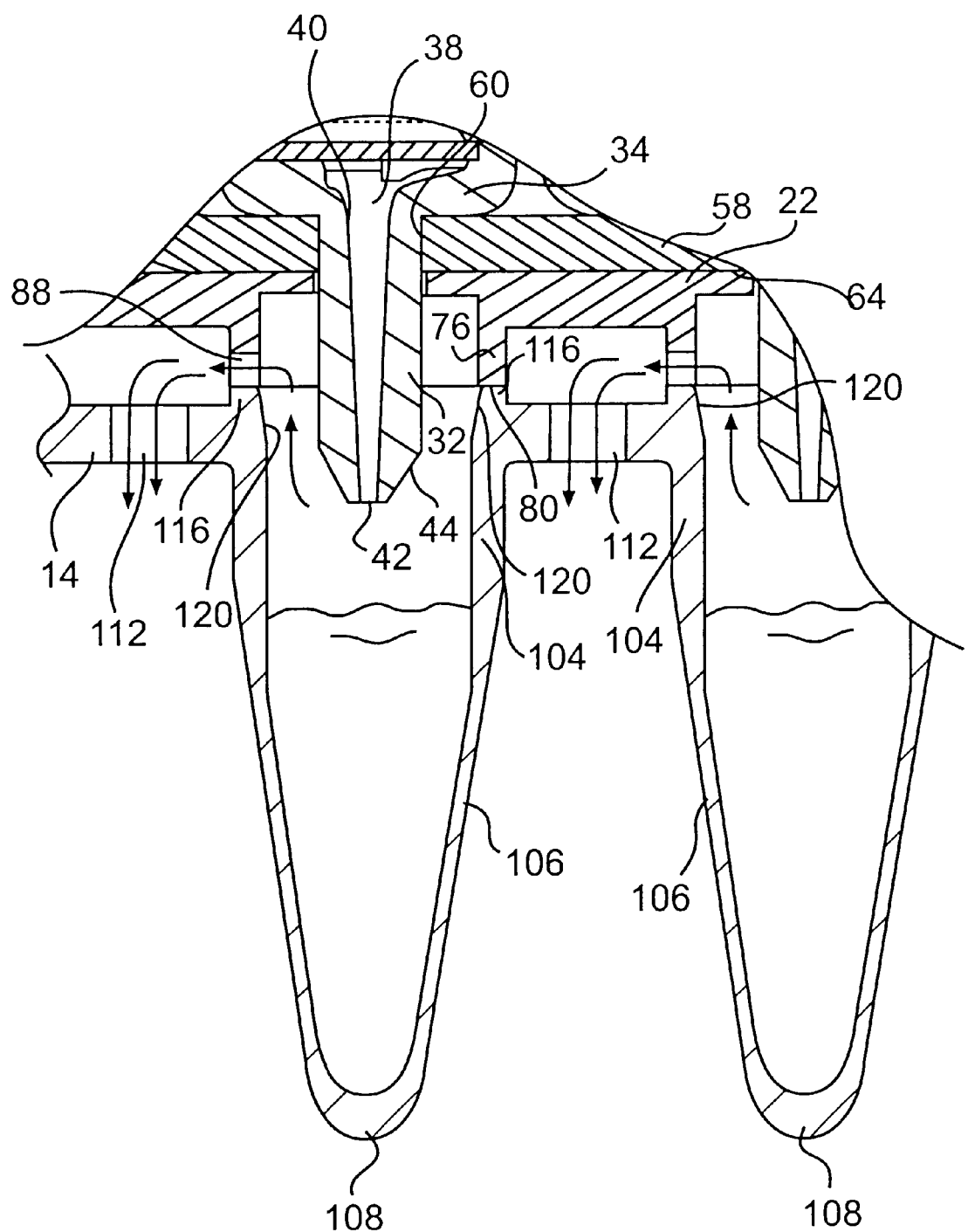
FIG. 8 is a close-up section view of the purification tray and sample well tray in an assembled state along line VIII—VIII of FIG. 16, with the section view passing through a notch in an aerosol guard and through an aerosol discharge aperture of the sample well tray.

The diameter of the inner surface of the tapered floor portion 36 progressively decreases in the downward direction from the flat outer annular surface 35, as best shown in FIG. 7. The tapered floor portion defines a hole 38 at the top of the drip director 32. The annular connecting portion 34 has a flat bottom surface 39. The flat bottom surface 39 extends substantially perpendicular to the first tapered cylindrical portion 30. The drip director 32 of the columns 28 extend in the longitudinal direction of the column (substantially perpendicular to the annular connecting portion 34). As best shown in FIGS. 7–8, in one embodiment, the drip directors 32 have a tapered inner cylindrical surface 40 which narrows progressively farther from annular connecting portion 34. The specific size of the end opening 42 and the taper of the inner cylindrical surface 40 inhibits fluid from flowing out of the drip directors unless a pressure differential is created between the top and bottom of the purification tray, as will be described below.

As embodied heroin and shown for example in FIGS. 6–8 the tip of each drip director 32 may include a chamfer 44 on the outer surface. The chamfer 44 on the outer tip surface is helpful in removing drops of liquid from the end opening 42, also called "touching off," when the purification tray is lifted from the sample well tray. This "ouch off" operation will be discussed in greater detail later in the specification, particularly in relation to a corresponding chamfer which may optionally be provided on the inside of a mating sample well surface. Alternately, the sample well tray may be touched off even there are no chamfers on the tip of the drip director or on the sample well surface, although chamfers are preferred in order to optimize the touching off operation.

In one embodiment, the columns 28 of the filter plate are connected toward a top portion thereof, as best shown in FIG. 6. The columns become separated toward a bottom portion of the first tapered cylindrical portion 30 adjacent the filters 18. Alternately, the first tapered cylindrical portions 30 of adjacent columns may be formed as a solid unit. The advantage of a solid configuration is that the columns will be more likely to maintain a constant distance between themselves. In another possible configuration, the columns could be discrete units that are not connected to one another at all. In such a configuration, each of the columns could be an individual tube that is either integrally attached to the filter plate, or could be separately detachable from the filter plate. In another possible configuration, the columns could be arranged in discrete strips. With a discrete strip, each column in the strip could be connected to the adjacent column in the strip by a web. A plurality of strips could then be arranged side-by-side within a frame designed to hold such strips. For example, twelve 8-well strips could be placed side-by-side in a rectangular frame to form a 96-well array.

The filter plate of the purification tray is preferably constructed of a substantially rigid, water insoluble, fluid impervious material that is substantially non-reactive with the fluid samples. The filter plate material should preferably resist deformation or warping under a light mechanical or thermal load, but may be somewhat elastic. In one embodiment, it is desirable that the filter plate material be able to withstand temperatures between 5 deg. C to 90 deg. C. In other embodiments, the temperature ranges may be significantly lower. In one preferred embodiment, the filter plate is made out of polypropylene. Other suitable materials include, for example, acrylics, polycarbonates, and polysulfones. Alternately, the fluid contacting surfaces of the drip directors 32 and first tapered cylindrical portion 30 may be formed out of, or coated with, a material that renders the surfaces hydrophobic. This type of material reduces the potential for cross-contamination. The filter plate may be made by any conventional method. One common method that is particularly suitable with the present invention is injection molding.

The filter plate may be a variety of sizes and shapes. In one preferred embodiment, the columns have a fluid volume of at least 1 ml. In another embodiment, the fluid volume may be significantly less or greater. In one exemplary embodiment, the top surface of the top plate portion has a length of 5.03 inches and a width of 3.37 inches. The top plate portion 24 may alternately include downwardly extending side walls 37, as shown for example in FIGS. 1–2, 4 and 6. The side walls 37 may be utilized to form a seal with a housing so that a pressure differential may be created between the top and bottom of the filter plate in a manner that will be described in greater detail later in the specification.

In one embodiment, the side walls 37 extend perpendicular to the top surface of the top plate portion 24 in a downward direction. In one example of this embodiment, the side walls have a height of 0.36 inches. In this embodiment, the distance from the top surface of the top plate portion to the ends of the drip directors is approximately 1.33 inches. The cylindrical openings 26 have an inside diameter of 0.312 inches. These dimensions are for purposes of illustration only, and are not limiting of the present invention.

In accordance with the present invention, the purification tray typically includes a plurality of filters. As embodied herein and shown in FIGS. 4 and 7, a filter element 18 is positioned in the columns 28 of the filter plate for filtering the fluid samples as the fluid passes through the filter element. The filter element may be placed in some or all of the columns. The filter elements are typically in the shape of a disc which closely corresponds in diameter to the inside diameter of the first tapered cylindrical portion 30 adjacent the annular rim 34. In one embodiment best shown in FIG. 7, the filter elements 18 are inserted into the cylindrical openings 26 of the filter plate and positioned so that they abut the flat outer annular surface 35 of the annular connecting portion 34.

It is desirable for the filter element to only contact the annular connecting portion at a small area, such as at the flat outer annular surface 35, so that the filter element 18 can effectively filter liquid through a substantial percentage of the filter element surface area. This allows the majority of the filter element's lower surface to be open and for substantially unobstructed flow to occur through the filter element. Because the flat outer annular surface 35 is specifically designed to have a very small width (outer diameter minus the inner diameter), the portions of the filter element 18 that abut the flat outer annular surface 35 are minimized. This promotes the effective flow of the liquid sample through the filter element and minimizes the amount of dead volume in the filter. The use of a small vacuum to pull the liquid through the filter element is preferable to the conventional method of centrifugation as regards minimizing these dead volumes. Dead volumes are volumes of the filter element through which the fluid samples do not pass efficiently through, i.e., which are not washed efficiently, often leaving contaminants. The specific design of the present invention minimizes these dead volumes.

Figure 11:
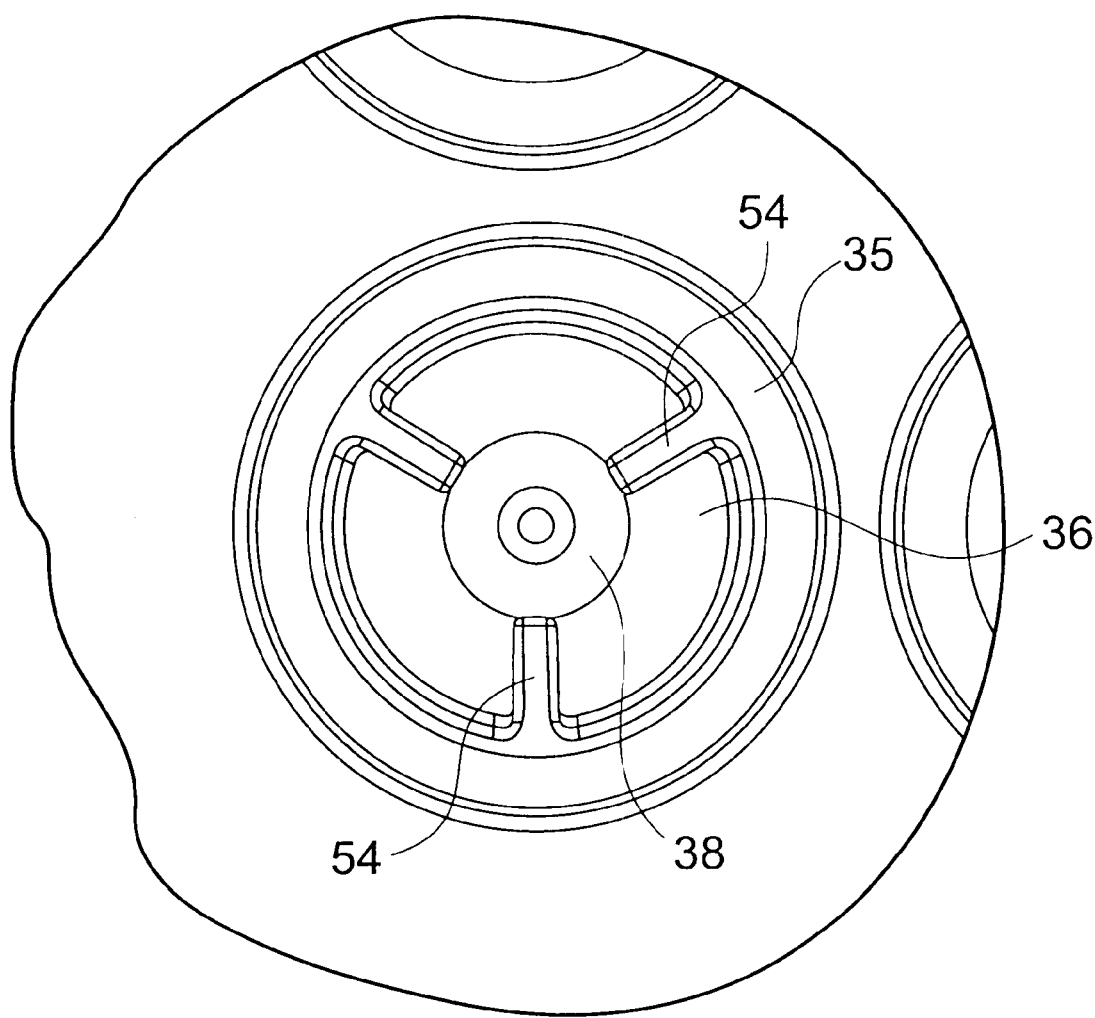
FIG. 11 is a top view of a column of the purification tray of FIG. 9 with the filter removed.
Figure 12:
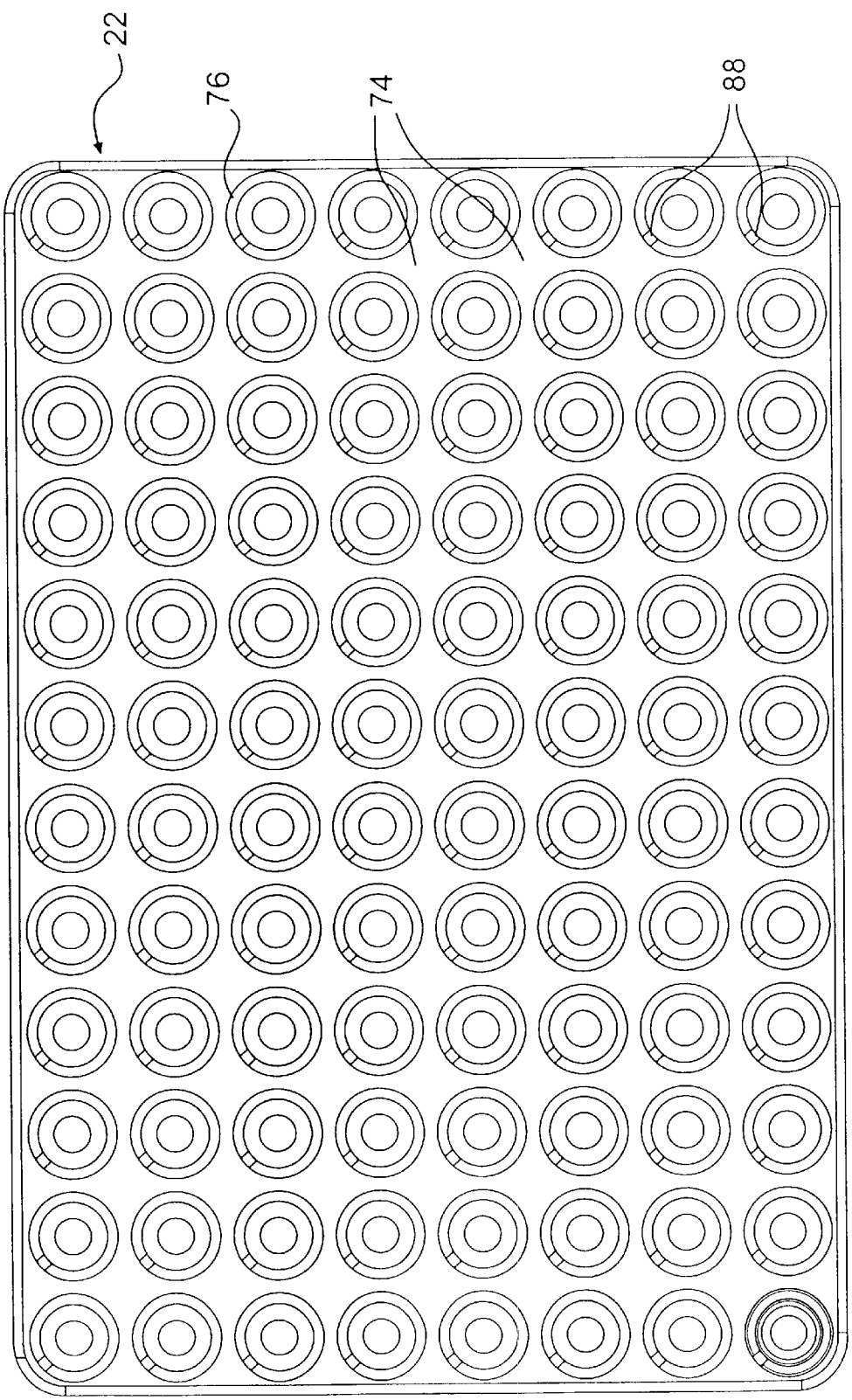
FIG. 12 is a bottom view of an aerosol guard of the purification tray of FIG. 1.
Figure 13:
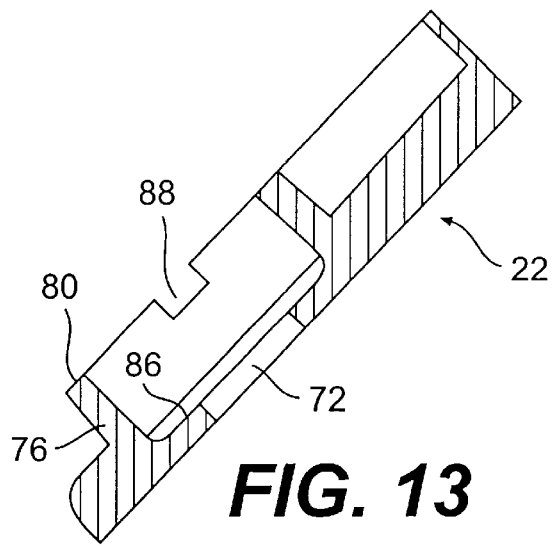
FIG. 13 is a partial side sectional view of the aerosol guard of FIG. 12.
Figure 14:
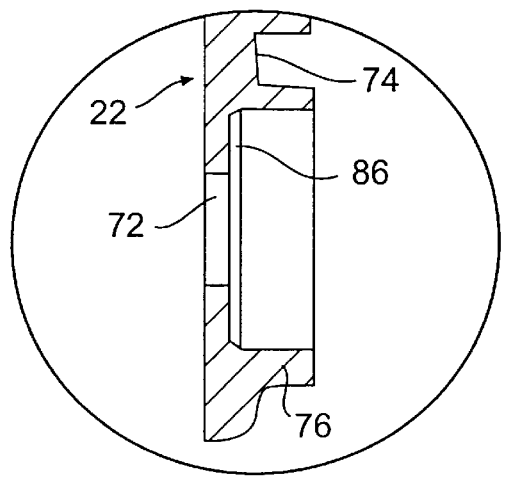
FIG. 14 is another partial side sectional view of the aerosol guard of FIG. 12.
Figure 15:
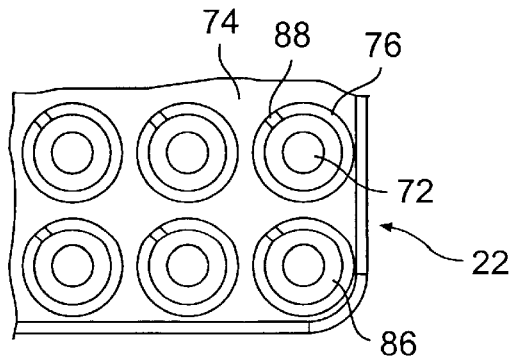
FIG. 15 is a partial bottom view of the aerosol guard of FIG. 12.

Having a large area of unsupported filter element bottom surface may lead to sagging or dislodgement of the filter element 18 into the hole 38 of the drip director 32. To minimize the potential of sagging or dislodging, the present invention in one embodiment provides structure for supporting central portions or regions of each filter element. For example, as shown in FIGS. 7 and 11, the annular connecting portion 34 may include a plurality of support buttresses 54. In the embodiment best shown in FIGS. 7 and 11, the support buttresses 54 project radially inward from the flat outer annular surface 35 of the column. The support buttresses provide a surface for the central portion of the filter element to rest against, thereby preventing sagging or dislodgement of the filter element. The support buttresses may be horizontal, or they may be tapered downward toward the center of the column so that the filter element only engages the support buttress during significant sagging.

Although FIG. 11 shows an embodiment with three of these support buttresses 54, any other suitable number of support buttresses may be included. In the illustrated embodiment, the support buttresses 54 are formed integrally with the column 40. Alternately, a plurality of discrete support buttresses, formed independently of the columns, may be removably positioned or permanently affixed within the columns.

In the embodiment best shown in FIGS. 7–8, the filter elements 18 are pressed down into the columns by filter retaining rings 50. The filter retaining rings 50 are annular members with an opening in the center thereof. The opening in the center of the filter retaining rings is preferably sufficiently large so that the filtering is not substantially hindered by the retaining ring. The filter retaining rings 50 are provided so that the filter elements 18 may be pressed firmly against the flat outer annular surface 35 of the annular connecting portion 34, as best shown in FIG. 7. The provision of the retaining rings also allows the filter element to be made relatively thin.

The filter retaining rings 50 are preferably made out of a more rigid material than the filter elements 18 so that the filter retaining rings may be pressed firmly against the inner surface of the first tapered cylindrical portion 30. In the embodiment shown for example in FIG. 7, the retaining ring has a curved inner surface 52 with a smaller inner diameter in the center than at the top and bottom portion thereof. Therefore, the amount of surface contact between the bottom of the filter support ring 50 and the filter element 18 is minimized, promoting enhanced flow through the filter element 18.

The filter retaining rings are typically configured to be engaged with a tool for inserting the filter retaining ring and filter element into the columns. The tool for inserting the filter retaining ring and filter into the columns may be automated or manual. Because the filter retaining ring is typically much stronger than a conventional filter element, a greater amount of force may be used to press down on the filter retaining ring than could be used with a conventional filter element by itself.

The material and type of filter element depends on the intended use of the purification tray and sample well tray. For example, the filter element might serve as a size exclusion filter. Alternately, the filter element could serve as a solid phase interacting with a species in the liquid phase to immobilize the species upon contact, such as an immunological interaction or any other type of affinity interaction. Examples of suitable filters include, but are not limited to, those of nitrocellulose, regenerated cellulose, nylon, polysulfone, glass fiber, blown microfibers, and paper. Additional examples of suitable filters include microfiber filters of ultra-pure quartz (SiO2). In another embodiment, the filter element is a porous element that acts as a frit, serving to contain a column packing material.

In the filter plate of the present invention, filters having a wide range of thicknesses may be accommodated in the columns. In the preferred embodiment shown in the Figures, filter elements having thicknesses of up to 2 mm thick may be used in the columns. Alternately, the filter elements used with the present invention may also be made very thin because of the provision of the filter retaining ring.

Although the illustrated embodiment shows filter retaining rings being pressed down on filter elements, the present invention may also be used without filter retaining rings. In such a scenario, it is preferable that the filter element be made out of a substantially rigid material so that the filter elements can be manipulated and positioned inside the columns. In either case, the filter element or retaining ring is preferably dimensioned so that it closely fits the inside diameter of the column when it is fully inserted into the first tapered cylindrical portion 30. The presence of a gap between the outer surface of the filter element or retaining ring and the inner surface of the column may result in liquid sample flowing around the filter without being filtered. This may result in undesirable contamination of the liquid sample in the sample well tray. A tight fit between the outer diameter of the filter element or retaining ring and the inner surface of the column also minimizes the possibility of the filter or retaining ring becoming disengaged from the inner surface of the column. Therefore, a tight fit is preferred.

The filter plate, filter elements, and retaining rings of the present invention described above are configured for minimizing the dead volume of the filter. The present invention assists in minimizing or eliminating contamination from occurring in the filter and ensures a smooth flow of the liquid sample through the filter. Other factors such as the pressure differential between the top and the bottom of the purification tray, the thickness and type of filter element, and the specific type of liquid sample also affect the amount of filter dead volume and contamination.

In accordance with the present invention, the purification tray includes a heat transfer plate for transferring heat to the liquids in the columns of the filter plate. As embodied herein and shown in FIGS. 1–20, the heat plate 20 includes a flat bottom portion 58 with a plurality of circulars apertures 60 for the drip directors 32 of the filter plate, as best shown in FIGS. 4 and 7. The openings 60 align with a corresponding drip director and are sized to closely mate with the drip directors 32 that pass therethrough. The inner cylindrical surface of the heat plate apertures 60 engage with the outside surface of the drip directors 32 as best shown in FIGS. 6 and 7. The close mating of the drip directors with the apertures 60 of the heat plate assists in maintaining the drip directors at equal spacing from one another. The equal spacing of the tips of the drip directors is particularly desirable for touching-off pendent drops from the tips of the drip directors during removal of the purification tray from the sample well tray. The close mating between the heat plate and the drip directors also helps to minimize any bending that might occur in the columns of the filter plate.

As shown in FIGS. 6 and 7, the filter plate is positioned on the heat plate 20 so that the flat bottom surface 39 of the annular connecting portion 34 engages the top surface 62 of the flat heat plate bottom 58. The heat plate may be attached to the filter plate by a variety of methods. In one embodiment, the heat plate is secured to the filter plate with a single screw passing through a hole 65 in the bottom of the heat plate, as shown in FIG. 4. Another method which is suitable for attaching the heat plate to the filter plate is adhesive bonding with an adhesive material that can withstand high temperatures. The heat plate may alternately be attached to the filter plate by use of fasteners, clamps, or any other suitable means. Alternatively, the heat plate could be co-molded into the filter plate or vent plate of the purification tray.

In the embodiment shown in FIGS. 1–20, the heat plate 20 further includes side walls 66. The side walls extend perpendicular from the flat bottom portion 58 of the heat plate. Preferably, the side walls are of sufficient height so that the columns of the filter plate are substantially covered. In the embodiment shown for example in FIG. 6, the side walls 66 extend upward into a region 68 provided around the bottom of the filter plate circumferentially inside of the downwardly extending filter plate side walls 37. The heat plate assists in promoting a substantially uniform temperature of the filter plate columns. In order to provide substantially uniform temperatures, the heat plate is made out of a thermally conductive material such as aluminum. A heating source (to be described later) provides heat to the heat plate.

The heat plate may be any size and shape suitable for heating a purification tray according to the invention. In one exemplary embodiment, the bottom 58 of heat plate has a length of 4.58 inches and a width of 3.04 inches. In the embodiment, the heat plate sidewalls 66 have a height of 0.80 inches, and the heat plate has a thickness of 0.062 inches. These dimensions are by way of example only and are not meant to limit the invention in any way.

As previously mentioned, the provision of the heat plate allows the purification tray of the present invention to be used for a wider range of filtration processes than the typical purification tray. The heating plate is shown for purposes of example only. It should be understood that alternate heating systems may be used be sides the heat plate shown in the Figures. For example, instead of needing a separate heat source for providing heat to the heat plate, the heat plate itself could be a heat source. One method would be to mount a resistive element heater on or in the heat plate. This would allow the heat assembly to be controlled with a higher degree of accuracy. With a resistive heater, the heat plate could include a plurality of distinct heating pieces that could be individually controlled. Alternatively, a foil heater could be used in order to provide a heat plate with distinct heating areas. With a foil heater, the power output for each distinct heating area may be varied. Alternatively, other methods for applying heating elements to a heat plate may also be provided, such as printing the heating of elements onto a heat plate or embedding a heat element within a plastic plate. By way of example only, other alternative heating systems include, for example, use of convective air flow, use of a liquid bath, and use of irradiant light to provide heat to the liquid in the columns of the purification tray.

In accordance with the present invention, the purification tray further includes a vent plate for permitting aerosols from the sample wells to escape. The vent plate is also referred to as an aerosol guard. As embodied herein and shown in FIGS. 1–20, the vent plate 22 for permitting aerosols to escape from the sample wells is positioned below the heat plate. Vent plate 22 includes a top surface 70, as best shown in FIG. 4. The top surface 70 is substantially flat with a plurality of openings 72 aligned with the columns 28 of the filter plate. In the example shown in the Figures, the vent plate openings 72 are arranged in a rectangular array matching the rectangular array of the filter plate columns. For example, in the embodiment shown in the Figures, the vent plate openings are arranged in a 8 by 12 array so that there are 96 openings. As best shown in FIGS. 6 and 7, the vent plate openings 72 have a diameter approximately equal to the diameter of the heat plate openings 60 and are located immediately adjacent the heat plate openings.

The top surface 70 of the vent plate 22 is preferably attached to the bottom surface 64 of the heat plate, as best shown in FIG. 7. The top surface 70 may be attached to the bottom surface 64 of the heat plate by any conventional method known in the art, such as adhesive bonding.

The vent plate is preferably made out of a substantially rigid or compliant material that is capable of withstanding the high temperatures associated with the heat plate. The vent plate material should be non-porous so that the aerosols only flow through the desired passages. The vent plate material should be substantially nonreactive with the chemicals used in the liquid sample. Polymers are particularly wellsuited for the vent plate. Alternately, the vent plate could be made out of foam-like material, however foam-like materials suffer from the disadvantage of being porous and typically unable to withstand high temperatures.

The bottom surface 74 of the vent plate 22 includes a plurality of cylindrical projections 76 extending downward therefrom, as best shown in FIG. 6–7 and 12–17. Each cylindrical projection 76 has a outer surface 78, a bottom annular surface 80, and an inner cylindrical surface 82. The inner cylindrical surface 82 defines the diameter of a circular cavity 84 in the bottom of the vent plate. The circular cavity 84 is further defined by an annular portion 86, as best shown in FIG. 7. In the embodiment shown in the Figures, the vent plate has a smaller thickness at the annular portion 86 compared to the thickness at the bottom surface 74. Alternately, the annular portion 86 could be removed so that the bottom surface 64 Of the heat plate serves as the top of the cavity 84. In such an arrangement, the vent plate openings 72 would have a diameter identical to the inside diameter of the cylindrical projections 76.

Each of the cylindrical projections 76 includes at least one notch or passage 88 passing from the inner cylindrical surface 82 to the outer surface 78. In the embodiment shown in FIGS. 1–20, a notch 88 is formed in the bottom annular surface 80 of the cylindrical projection. The notch is shown as being square, however, any other suitable geometric shape such as circular or triangular is also acceptable. Alternately, the notch could be replaced by a passageway passing through the cylindrical projection 76. Although the embodiment shown in the Figures only shows one notch for each cylindrical projection, more than one notch may also be provided. The purpose of the notch will be described in relation to the sample well tray described below.

Figure 19:
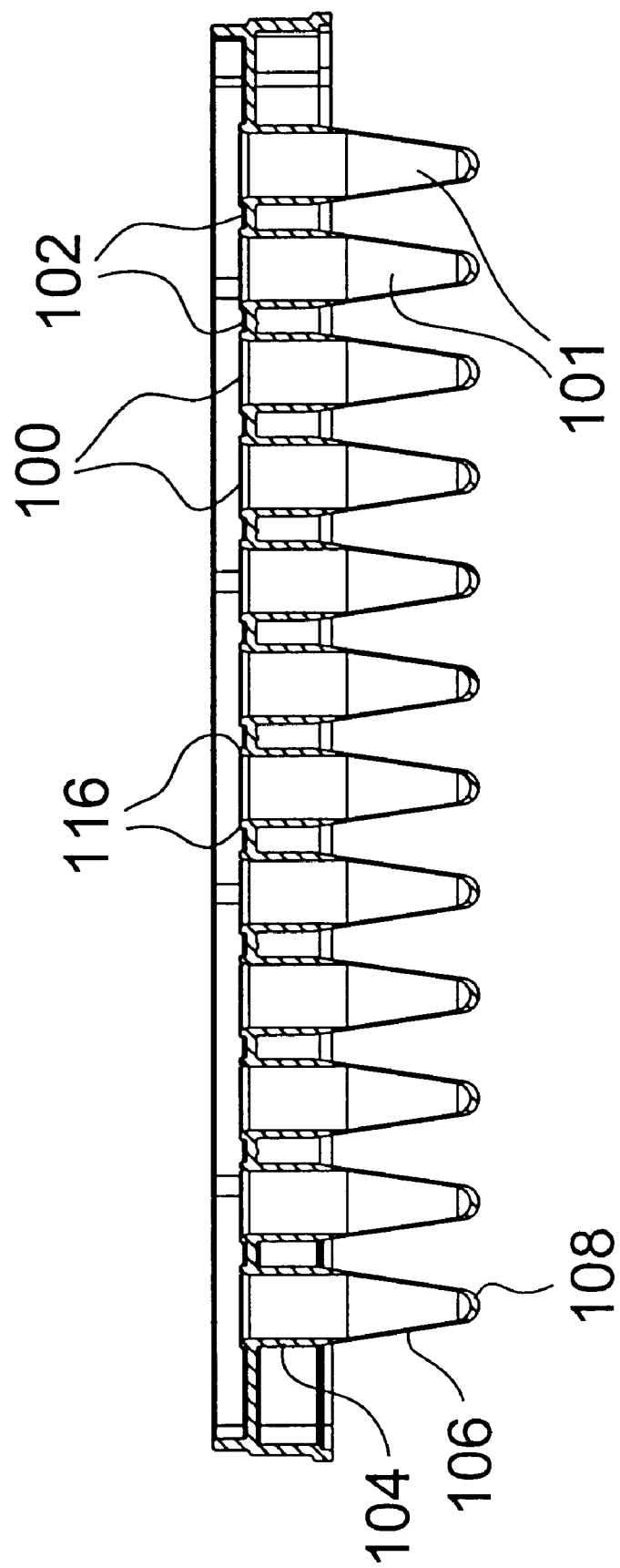

In accordance with the present invention, the purification tray is typically used in combination with a sample well tray. The sample well tray is positioned below the purification tray so that the liquid sample is filtered through the filters and received by the sample wells of the sample well tray. As embodied herein and shown in FIGS. 1, 3, 18, and 19, in one embodiment, the sample well tray 14 includes a plurality of sample well openings 100 in a top surface 102 thereof to define sample wells 101. The sample wells are typically configured in a rectangular array such as the 8 by 12 array shown in the Figures. The arrangement of sample wells preferably matches the arrangement of drip directors from the purification tray. As shown in FIGS. 8 and 19, the sample wells 100 are defined by a top cylindrical section 104, a conical section 106, and a rounded bottom section 108. The shape shown in the drawings purposes of example only. The sample wells may be of a variety of shapes such as conical, cylindrical, or hemispherical. The specific shape of the sample wells may be any suitable design.

Each sample well 100 can hold a predefined volume of liquid sample. The volume and dimensions of the wells varies depending on the intended use of the sample well tray, as well as the number of sample wells that are provided. For example, a sample well tray with 384 wells will typically have smaller sample well volumes and dimensions. In the example shown in the drawings, the sample well openings 100 have an inside diameter of approximately 0.23 inches. The sample wells 101 have a depth (from top surface 102 to rounded bottom surface 108) of approximately 0.82 inches. These dimensions are for purposes of illustration only.

The sample well tray may be designed so that it is larger than or smaller than the purification tray. In the embodiment shown, for example in FIG. 1, the sample well tray is designed to be approximately the same size as the top plate portion 24 of the purification tray. In one example, the top surface 102 of the sample well tray (including the upwardly extending rim 110) is approximately 3.38 inches in width and 4.96 inches in length.

The sample well tray further includes a plurality of aerosol discharge apertures 112 passing through the top surface thereof. The aerosol discharge apertures 112 shown in FIGS. 1, 3, 8 and 18 are arranged in a rectangular array. The aerosol discharge aperture array is a 9 by 13 array in the example shown. The aerosol discharge apertures 112 are placed at the same intervals as the sample well openings 100. The apertures 112 are positioned so that they align with the notches or vents 88 in the vent plate as will be discussed below. In one example, the aerosol discharge apertures have a diameter of 0.091 inches.

In one embodiment, the sample well tray may further include cylindrical raised projections 116 around each of the sample well openings 100, as best shown in FIGS. 8 and 19. The cylindrical raised projections are raised above the top surface 102 by only enough to form a sealing surface with the vent plate. The cylindrical raised projections 116 align with the cylindrical projections 76 of the vent plate as will be described below. In other alternative embodiments, the sample well tray does not include cylindrical raised projections 116, so that the cylindrical projections 76 of the vent plate abut with the top surface of the sample well tray. However, it is preferable to include the cylindrical raised projections 116.

During filtering operations, the purification tray is placed on top of the sample well tray so that the drip directors 32 are centered in the sample well openings 100 as best shown in FIGS. 6 and 8. As shown in FIG. 8, the bottom annular surface 80 of the cylindrical projection 76 is positioned so that it abuts the corresponding cylindrical raised projection 116 of the sample well tray. Because the bottom annular surface 80 is pressed against the sample well tray cylindrical raised projection 116, substantially no gases may exit the sample wells except through the vents or notches 88.

Figure 16:
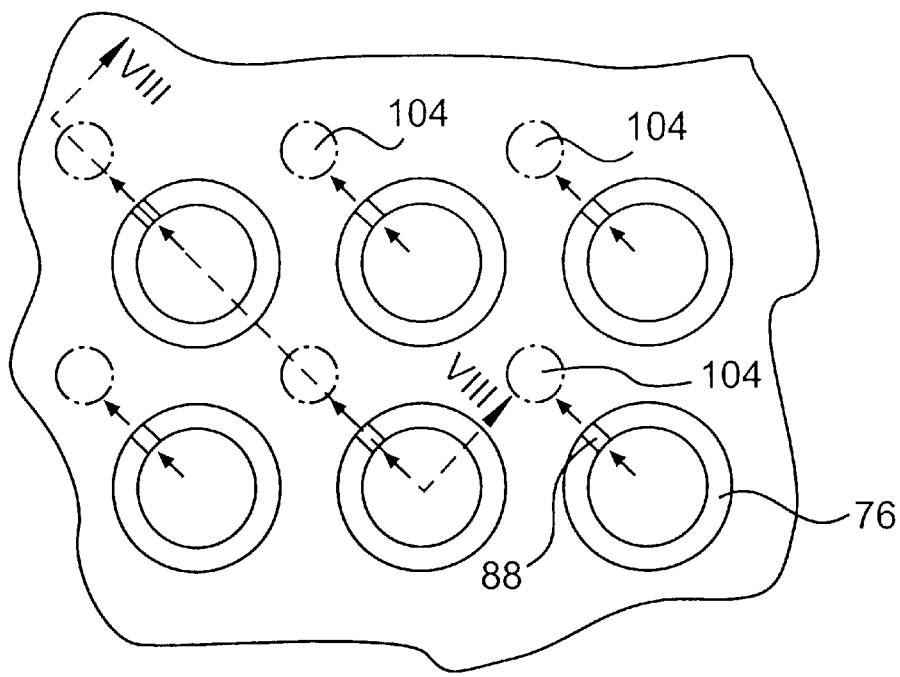
FIG. 16 is a schematic illustrating the alignment of notches of the aerosol guard with aerosol discharge apertures of the sample well tray.
Figure 17:
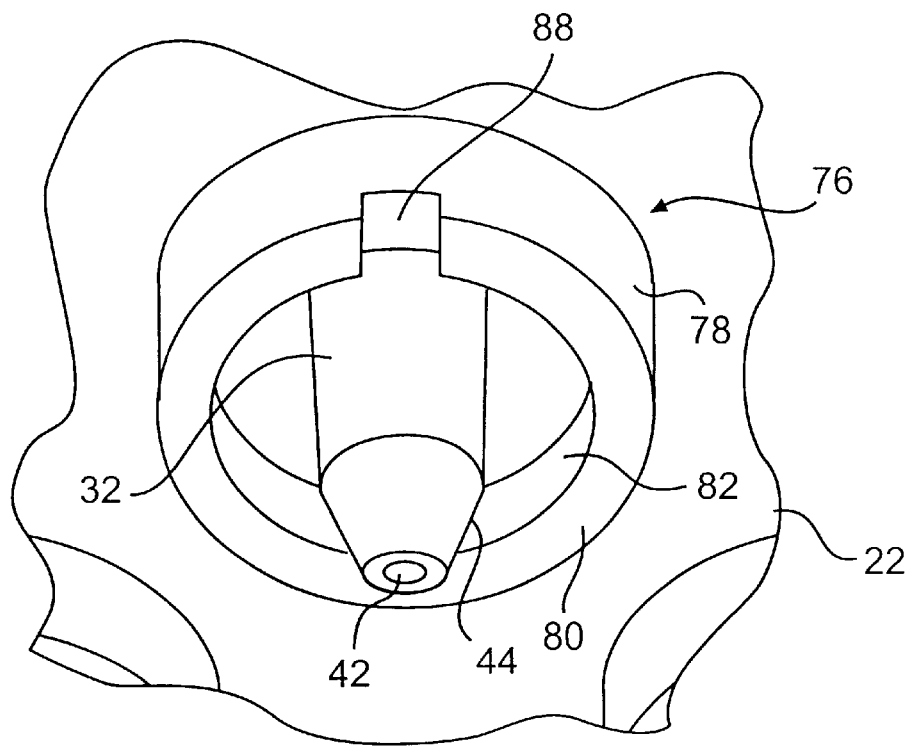
FIG. 17 is a partial bottom perspective view of a drip director projecting from the aerosol guard of the purification tray of FIG. 1.
Figure 18:
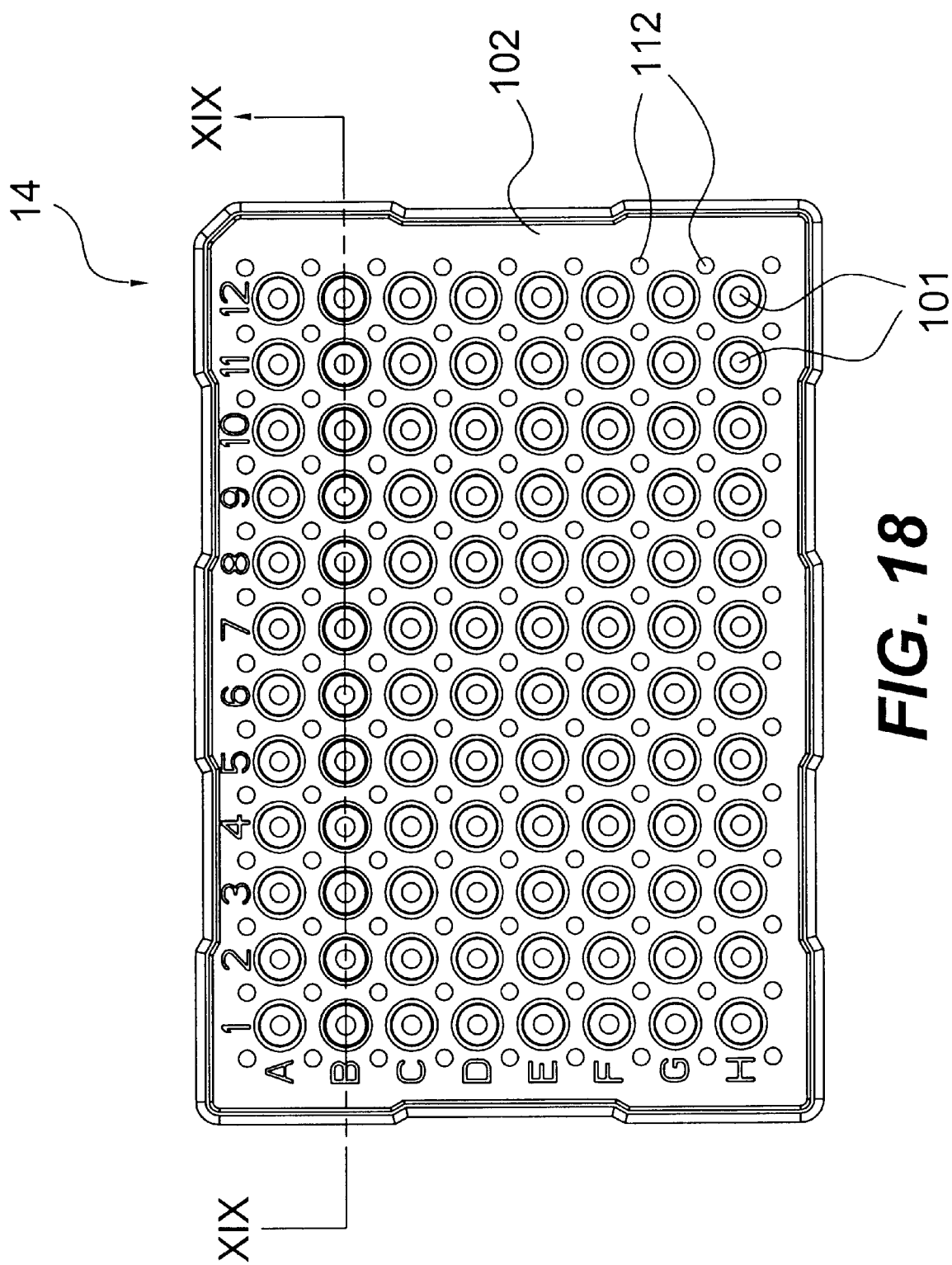

FIG. 16 is a schematic illustrating the arrangement of the aerosol discharge apertures 112 of the sample well tray relative to the vent or notches 88 of the vent plate tray. FIG. 16 is drawn along two different sections in order to illustrate that the aerosol discharge apertures of the sample well tray are aligned with the notches so that gases in a sample well may exit the sample well and be guided to an adjacent aerosol discharge aperture 112. As previously discussed, gases and aerosols are created in the sample wells during filtration of the fluid sample through the filter and during the subsequent filling of the sample wells with the fluid sample. The configuration of the vent plate of the present invention allows the gases formed in the sample wells to escape from the sample wells without contaminating an adjacent sample well. For example, as best shown in FIG. 8, the gases located above the liquid sample are allowed to escape from the sample wells by flowing through the vent 88 and then downward through the adjacent aligned aerosol discharge aperture 112. The pressure differential created by the vacuum chamber urges the aerosols to exit the sample wells in this manner.

Another alternative method for urging the liquid sample through the filter element, instead of using a lower vacuum chamber, is to use an upper pressure chamber. The upper pressure chamber could be sealed around the top of the purification tray. Preferbly, the upper pressure chamber would apply a slight pressure to the top of the purification tray to urge the liquid sample through the filter element and into the corresponding sample well Although the present embodiment shown in FIGS. 1–20 illustrates only one notch or vent for each of the sample wells, a plurality of notches may also be provided. If a plurality of notches are provided for each sample well, each of the notches should be provided with a corresponding aerosol discharge apertures. Therefore, additional aerosol discharge apertures may need to be provided in such an embodiment.

In accordance with the present invention, the sample well trays may also include sample well chamfers 120 on the inner surface of the sample wells adjacent the cylindrical raised projections 116, as best shown in FIG. 8. In the embodiment shown in FIG. 8, the sample well chamfers are angled outward to define a larger diameter than the rest of the sample well inner surface. The sample well chamfers 120 are helpful in promoting touching off of the drip directors as will be described below. During touching off, it is desirable to remove pendent drops of liquid sample from the drip director openings 42 so that the pendent drops are not mistakenly dripped into the wrong sample well when the purification tray is lifted and removed from the sample well tray. The dripping of a liquid sample that is not intended for the particular sample well may cause contamination of that well. This situation is preferably avoided.

After the fluid sample is filtered through the filter and passed into the sample well as described, pendent drops of liquid sample often remain fixed to the surface of the drip director opening 42. It is desirable to remove these drops from the tip of the drip director so that they leave the tip and fall into the sample well opening located immediately underneath the drip director, also referred to as "touching off" the pendent drops. The term "touching off" is often used to refer to the step in hand pipetting when the drops on the tip of the pipette are touched off into the inside of the collection tube. In this step of touching off, prior to complete removal of the purification tray from the sample well tray, the purification tray (and drip directors) is lifted from the sample well tray by a slight distance and then moved horizontally by a slight distance so that the drip director chamfer 44 will touch against the chamfer inside surface 120 of the sample wells. The touching of the chamfer 44 of the drip director 32 against the chamfer surface 120 of the sample wells urges the remaining pendent drops of liquid sample to drop into the sample wells. In a typical touching off step of the present invention, the purification tray is also moved in the opposite horizontal direction to touch the opposite surface of the same sample well. The provision of the sample well chamfered surface 120 promotes more thorough touching off of these pendent drops. Because the sample well chamfer is angled to match the angle of the sample well chamfer 44, the pendent drops on the bottom of the drip director are more likely to adhere to the inner surface of the sample wells and flow down into the sample well. This touching off operation is one means of avoiding cross contamination which can be caused by dripping of liquid sample into a non-aligned sample well during removal of the purification tray.

The other means of assisting in minimizing contamination caused by a potential dripping of pendent liquid sample drops into a non-aligned sample well is by the use of an upper vacuum chamber on top of the purification tray. The upper vacuum chamber can be of any type known in the art. In one typical design, the upper vacuum chamber (not shown in the Figures) is a rectangular plate with downwardly extending walls that closely correspond with the dimensions of the top of the purification tray. The upper vacuum chamber may be placed in a closed position where the vacuum chamber forms a substantially airtight seal with the top plate portion 24 of the purification tray. The hollow interior of the chamber may be pneumatically connected to an external vacuum source in order to reduce pressure above the sample wells in order to pull any pendent drops that still remain in the drip directors after touching off back into the filter element. This helps to ensure that the any pendent drops that remain will not be located in the vicinity of the drip directors. This operation occurs after the filtration procedure has already occurred. Another alternative method of minimizing the amount of pendent drops in the drip directors would be to provide pressure to the chamber below the purification tray. The pressure below the purification tray could push the pendent drops back into the filter elements in a manner similar to the use of an upper vacuum chamber.

During the filtration process, the upper vacuum chamber will be in an open position so that the air above the purification will be at an ambient pressure. Therefore, for purposes of describing the preferred method of filtering the liquid sample through the filter element, it should be assumed that the upper vacuum chamber is in the open position during the step of eluting the liquid sample through the filter elements. A second vacuum chamber, also referred to as the lower vacuum chamber below, will create the vacuum below the purification tray to assist in pulling the liquid sample through the filters. This second vacuum chamber also assists in creating a flow path for the aerosols in the sample wells to flow through the notches and downward through the aerosol discharge apertures in the sample well tray.

In accordance with the present invention, the purification apparatus includes a lower vacuum chamber for creating an area of reduced pressure below the filter elements 18 during the step of drawing the liquid sample through the filter elements. The lower vacuum chamber creates pressure differential between the top and bottom of the purification tray, so that the volume above the filter elements is at ambient pressure and the volume below the filter elements is subject to a vacuum. The pressure differential assists in pulling the liquid sample downward through the filter elements. The basic concept of creating a pressure differential to draw the liquid through a filter is known in the art.

In the specific embodiment shown in FIG. 20, the purification tray is placed in a carriage 150 with a lower vacuum chamber in the area below the purification tray aperture 152. In such an arrangement, the purification tray is placed in the rectangular aperture 152. As embodied herein and shown in FIG. 20, in order to create a seal between the top and bottom of the purification tray, the downwardly extending walls 37 of the filter plate 16 may be sealed with the inner walls of an opening such as rectangular aperture 152 of the carriage 150.

In one embodiment, the carriage 150 may be moved horizontally so that the purification tray can be moved between several different locations and then lowered down at each respective location. For instance, in one embodiment, the carriage is first placed at a first position where an initial flush is performed. The carriage may then be moved horizontally to a second position where a series of washes are performed. The carriage may then be moved to a third position which corresponds to the position where the purification according to the present invention takes place. In this third position, the purification tray is first moved horizontally so that the drip directors of the purification tray are aligned with a sample well tray of the present invention. The purification tray is then vertically lowered so that the purification tray is pressed down on the sample well tray and so that the carriage forms a lower vacuum chamber for the purification tray and the sample well tray. The sample well tray is typically located in a sample block for supporting the sample well tray. After a vacuum has been imparted in the lower vacuum chamber of the carriage, the filtration and simultaneous heating steps are undertaken. It should be understood that the present invention may also be used with a carriage that is stationary, although the preferred embodiment includes a carriage that may move between a plurality of positions.

The lower vacuum chamber typically includes a vacuum manifold positioned below the sample well tray in order to promote the flow of the aerosols through the vents and downward through the aerosol discharge apertures 112 of the sample well trays.

In accordance with the present invention, the purification apparatus may include a heater assembly for providing heat to the heat transfer plate. As embodied herein and shown in FIG. 20, the heater assembly 154 may be located in the carriage 150. The carriage shown in FIG. 20 includes the rectangular purification tray aperture 152 which closely fits the outside periphery of the purification tray. The heater assembly 154 provides heat to the purification tray that is inserted into the purification tray aperture 152 in a manner which will be described below. The heater assembly of the embodiment shown in FIG. 20 includes a cartridge heater 156 and rear housing 158. In this embodiment, the cartridge heater is a resistive-type heater having a metal tube with a wound coil inside. The cartridge heater includes a contact surface 160 for being pressed against the side walls 66 of the heat transfer plate 20. Other types of heaters are also suitable with the present invention.

Figure 20:
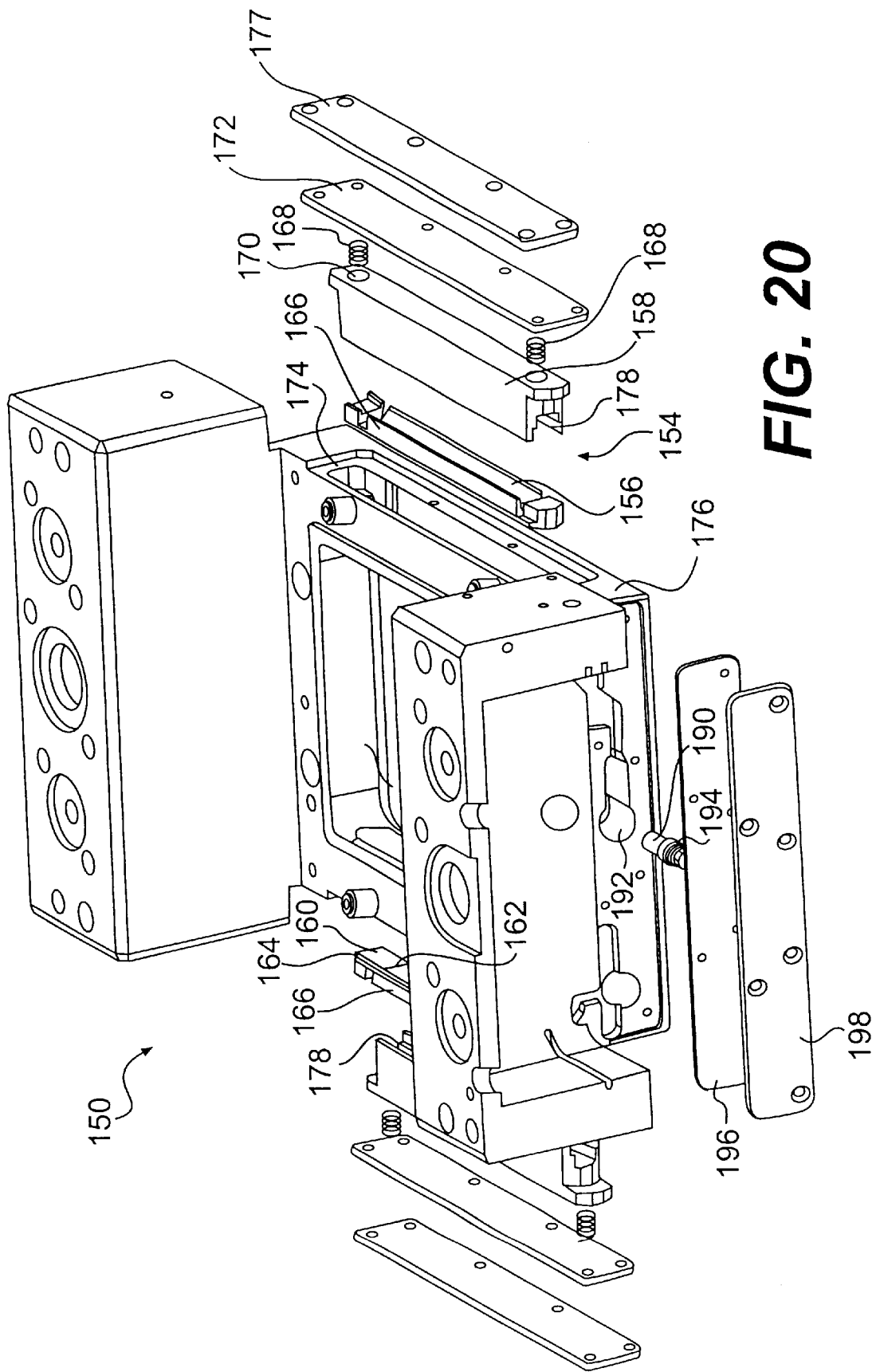

In one embodiment of the present invention, the contact surface 160 may include a plurality of grooves such as groove 162 shown in FIG. 20. Other grooves similar to groove 162 are spaced at predetermined intervals along the length of the cartridge heater in order to compensate for temperature irregularities of the heat plate. The grooves are typically positioned parallel to the groove shown in FIG. 20. Temperature irregularities occur on the heat plate due to the uneven temperatures experienced by the interior of the purification tray. In order to attempt to even out the temperature irregularities in the purification trays, the grooves are provided at positions along the cartridge heater at which it is desirable to have a lower amount of heat transfer relative to other portions of the cartridge heater. The amount of heat transfer that occurs at a location with a groove is less than the amount of heat transfer that occurs at a flat (ungrooved) portion of the cartridge heater because the cartridge heater will not contact the heat plate at the groove.

In the embodiment shown in FIG. 20, these grooves extend in the vertical direction. In one embodiment, each contact surface 160 of the cartridge heater includes six grooves. The number and configuration of grooves may be varied depending on the specific temperature characteristics of the purification tray.

The contact surface 160 may be designed to include chamfers 164 at a top portion of the contact surface as shown in FIG. 20. The chamfers 164 are angled so that during insertion of the purification tray into the rectangular apertures, the heat plate 20 of the purification tray will not get snagged on the cartridge heater 156. The chamfer is angled between the contact surface 160 and the top surface 166 of the cartridge heater to form a ramp for the heat plate as will be described below. The rear housing 158 of the heater assembly includes a plurality of spring members 168. In the embodiment shown in FIG. 20, the spring members 168 are coil springs that are positioned in spring apertures 170 in the rear housing. The coils springs 168 are biased against a first plate 172 at one end. The first plate is typically bolted to a corresponding rectangular groove 174 formed in an outer side wall 176 of the carriage. The first plate 172 may be covered by a second plate 177 as shown in FIG. 20 in order to enhance the seal and ensure the integrity of the lower vacuum chamber.

In the example shown in FIG. 20, the cartridge heater 156 is inserted inside a corresponding groove 178 of the rear housing 158. The coil springs 168 pass through the spring apertures 170 to engage the cartridge heater 156 and bias the cartridge heater towards the purification tray. The cartridge heater 156 is configured to be movable relative to the rear housing 158. The chamfers 164 of the cartridge heater are useful during insertion of the purification tray into the rectangular aperture 152. The chamfers allow the purification tray to ramp along the chamfer and push the cartridge heater horizontally away so that the purification tray may be adequately inserted into the rectangular aperture 152.

Because of the provision of springs 168, the contact surface 160 of the cartridge heater may be maintained substantially flush against the outer contact surface of the heat plate side walls 66 in order to provide substantially uniform heat transfer to the heat plate and purification tray. In order to enhance temperature uniformity, the rear housing 158 of the heater assembly is preferably made out of insulating material. This helps to direct heat toward the heat plate 20 and away from the carriage 150.

The contact surface 160 of the heat assembly is typically only heated during the portion of the process during which the biological sample is being filtered through the filter element. After the liquid sample is eluted into the sample wells, the heating assembly will typically be turned off so that no further heat is generated by the cartridge heater. The liquid in the sample wells is preferably immediately lowered to a very low temperature. In one embodiment, is preferable that the liquid sample is lowered to approximately four degrees celsius after the elution step.

It is desirable that the temperature of the purification tray be accurately monitored. In the embodiment shown in FIG. 20, the carriage 150 includes a temperature probe 190 such as a thermistor positioned in a temperature probe aperture 192. The temperature probe is engaged with a spring 194 so that the tip of the probe will be pressed against the side walls 66 of the heat plate 20. In the FIG. 20 embodiment, first and second plates 196 and 198 are used to cover the temperature probe 190. The temperature probe is used to measure the temperature of the heat transfer plate. Other types and designs for temperature probes besides that shown in FIG. 20 may be used with the present invention. The temperature probe of FIG. 20 measures the temperature of the heat plate. It is also desirable to be able to measure the actual temperature of the liquid sample in the purification tray. According to one alternate embodiment, a non-contact temperature sensor may be located above the purification tray in order to sense the temperature inside the purification tray columns. These temperature values will then be sent to a controller which controls the heater assembly. In another alternate embodiment, a temperature sensor may be located inside one of the columns of the purification tray.

In a further embodiment, a temperature sensor could be positioned directly on the heat transfer plate. In such an arrangement, the heat transfer plate could include a resistive or foil type heater so that no cartridge heater or external heating assembly would be required.

Although the embodiment above is described to include a heating plate and heater assembly, it should be understood that the purification apparatus has may benefits such as aerosol management and reduced likelihood of leaking, even if a heat plate and heater assembly is not included.

In a related aspect, the present invention provides a method of filtering liquid samples into sample wells in a sample well tray using a purification tray. According to one embodiment, the method includes providing a purification tray and sample well tray, the purification tray having a plurality of columns with discharge openings at the bottom thereof. Tho method further includes providing filters in the plurality of columns and introducing a liquid sample into at least one column of the purification tray so that the liquid sample contacts the filter in the column. Next, a pressure differential is applied to the column so that the liquid sample is urged through the filter and out of a discharge opening of the column into the sample well. The method further includes obstructing aerosols formed in the sample wells from mixing with the liquid sample of an adjacent sample well by providing an aerosol guard with a discrete flow path out of the sample well.

In another aspect, the present invention includes a purification apparatus of a second embodiment. In this embodiment, the apparatus includes a purification tray with a filter plate, a plurality of filters, a heat plate, and a vent plate. The purification tray is used in conjunction with a sample well tray. As embodied herein and shown in FIGS. 21–25, the purification tray 200 includes a filter plate 202 with a plurality of filters (not shown) located within the columns of the filter plate, a heat plate 204, and a vent plate 206.

Figure 22:
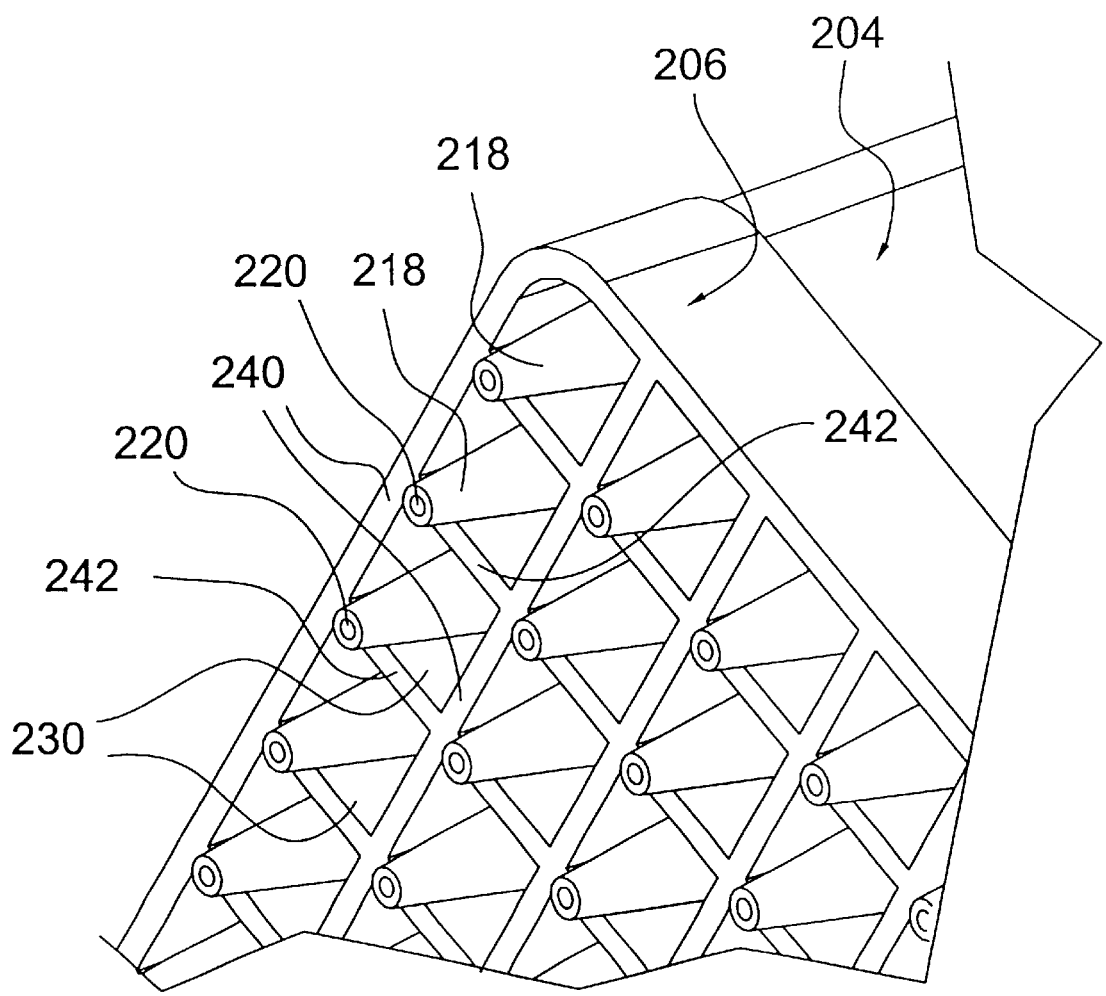
Figure 23:
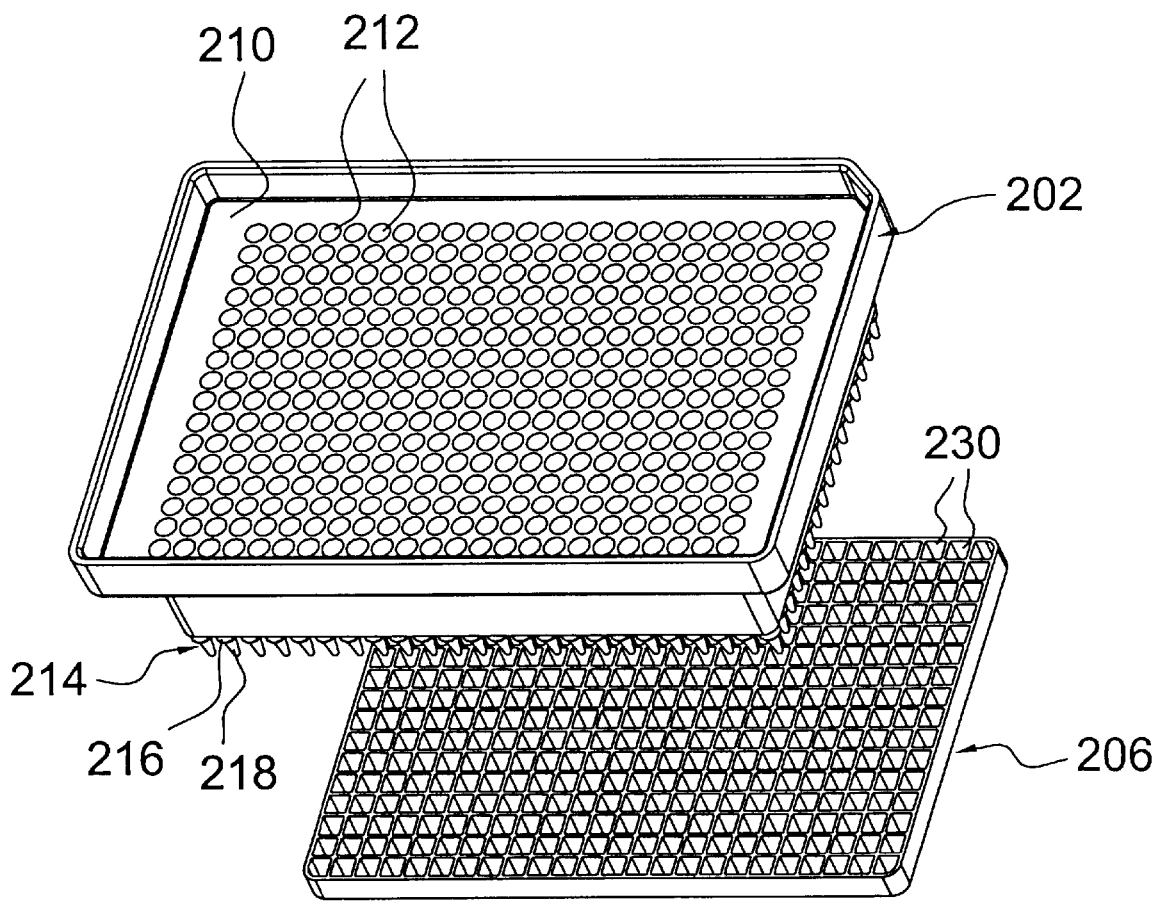
Figure 24:
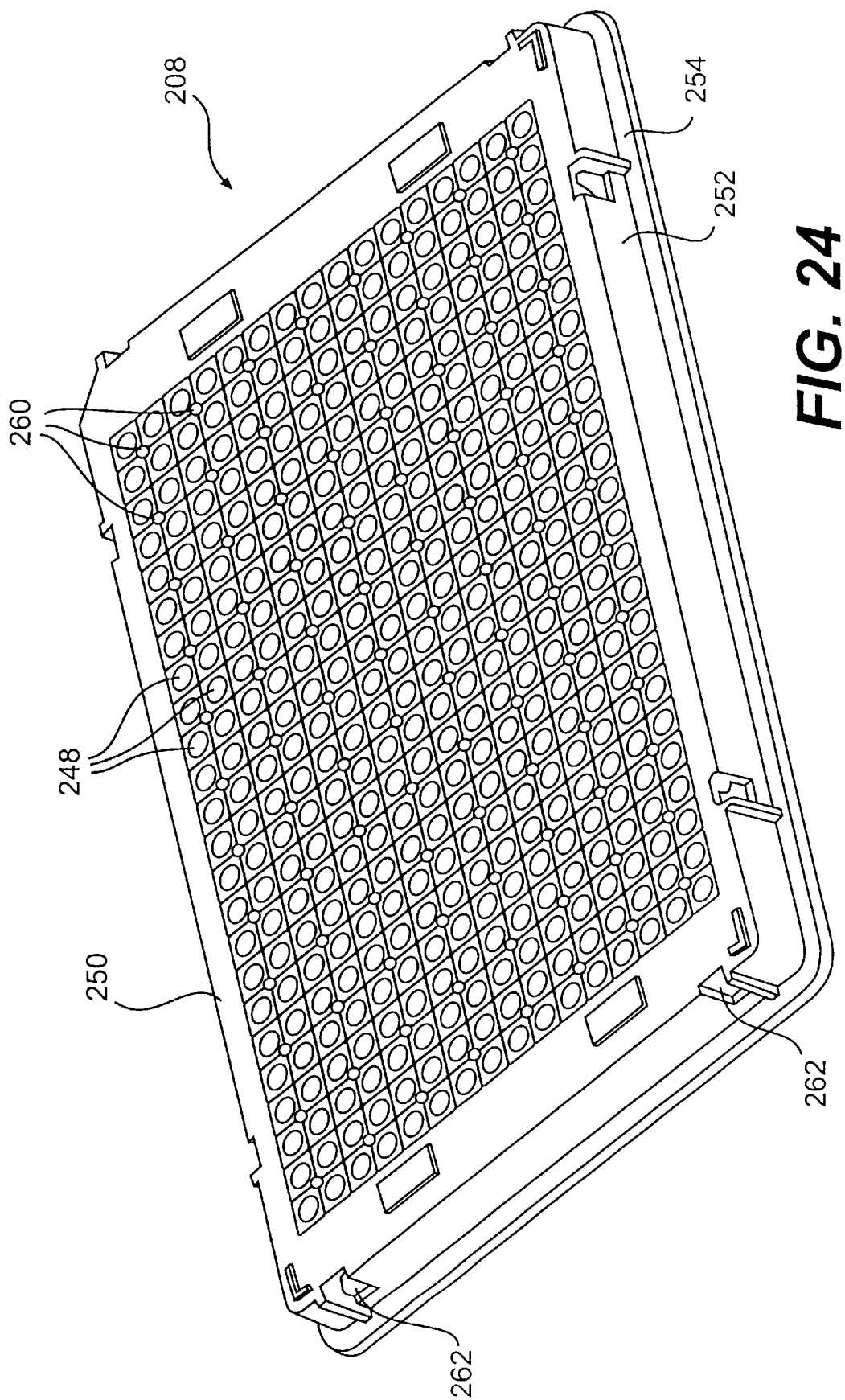

The purification apparatus of the embodiment shown in FIGS. 21–25 is suitable for use with a 384-well sample well tray such as sample well tray 208 shown in FIG. 24. The purification tray 200 is similar in many respects to the purification tray described in relation to FIGS. 1–20, but is adapted for use with a 384-well sample tray. The description of this embodiment will focus on the differences between the purification trays of this embodiment and the previous embodiment, and will not repeat substantially identical subject matter.

Figure 21:
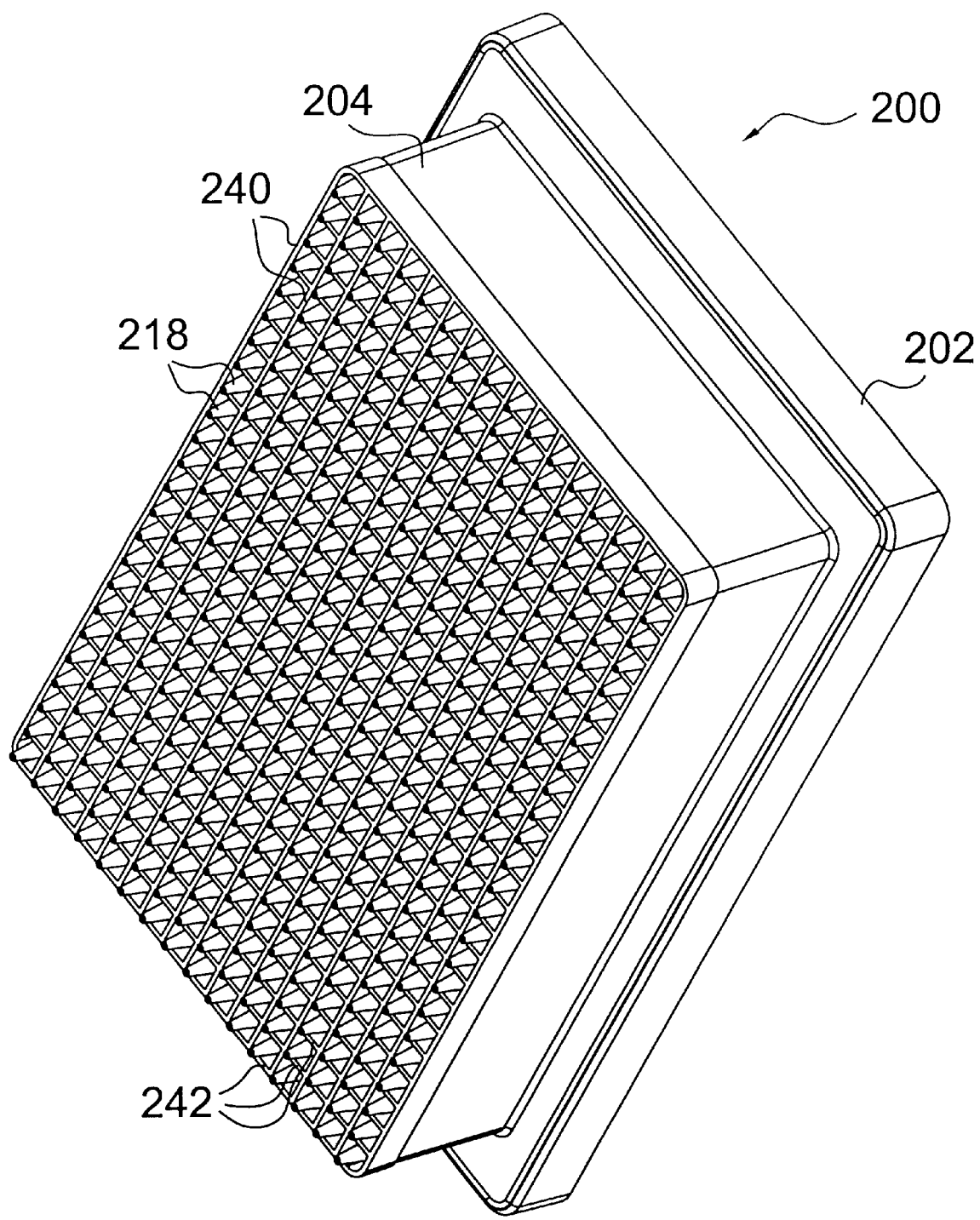

In accordance with the second embodiment of the present invention, the purification tray includes a filter plate with a plurality of columns with discharge openings near the bottom thereof. As embodied herein and shown in FIGS. 21–25, the filter plate 202 includes a top plate portion 210 with a plurality of cylindrical openings 212, as best shown in FIG. 23. Although FIGS. 21–25 show the filter plate having three hundred eighty-four openings, the present invention is suitable with any of the other common configurations, such as 96, 60, or other numbers. The filter plate (and corresponding sample well tray) of the present invention is also suitable with other configurations having any number of openings ranging from one to several thousand. In the 384-well embodiment, the openings in the filter plate are typically arranged in a 16 by 24 rectangular array.

The filter plate 202 includes a plurality of columns 214 extending downward from the top plate portion 210 of the filter plate, as beat shown in FIG. 23. The columns 214 may include an upper cylindrical portion 216 and a lower drip director 218. The upper cylindrical portion will accommodate filter elements similar to those described in FIGS. 1–20, but of smaller sizes. The drip director 218 is tapered in a similar manner to the drip director described in the FIGS. 1–20. The drip directors 218 have a drip director opening 220 at the tips thereof. The drip directors may have chamfered outer tips similar to those described in FIGS. 1–20 in order to enhance touching off of the drip directors.

In accordance with the second embodiment of the present invention, the purification tray includes a heat plate for providing heat to the columns of the purification tray. As embodied herein and shown in FIGS. 21–25, the heat plate 204 surrounds the periphery of the columns in a manner similar that described in FIGS. 1–20. The heat plate 204 preferably includes a bottom plate surface (not shown) with a plurality of apertures corresponding to the columns 214. The heat plate 204 transfers heat to the liquid sample in the columns during the step of filtering the liquid sample through the filter elements.

In accordance with the second embodiment of the present invention, the purification tray includes a vent plate for permitting aerosols from the sample wells to escape. As embodied herein and shown in FIGS. 21–25, the vent plate 206 includes a series of perpendicularly intersecting walls 240 and 242 extending in a grid-like fashion in order to define a plurality of rectangular vent apertures 230. A first set of parallel walls 240 extend in a first direction. A second set of parallel walls 242 extend in a second direction that is perpendicular to the first direction. The first and second set of walls intersect in the manner shown in the Figures to define a plurality of vent apertures 230. In the embodiment shown in FIGS. 21–25, the vent plate will have three hundred eighty-four vent apertures. The vent apertures are configured in a rectangular array to match the rectangular array of the drip directors. The vent plate is configured so that the drip directors 218 of the filter plate 202 extend through the vent plate and project from the bottom of the vent plate as shown in FIGS. 21 and 22. When the vent plate is positioned against a bottom surface of the heat plate, the vent plate defines a plurality of vent chambers for each of the openings. The bottom surface of the heat plate will substantially prevent aerosols from the sample wells from flowing out of the top portion of the vent openings 230. The vent chambers will also facilitate the flow of aerosols out of the sample wells in a manner which will be described below.

The purification apparatus of the present invention is used in conjunction with a sample well tray having a plurality of sample wells. As shown for example in FIG. 24, the sample well tray is a 384-well tray 208 with a plurality of sample well openings 248. The sample well tray is designed to be interchangeable with existing designs. The sample well tray includes a top flat surface 250, downwardly extending side wall 252, and flanged bottom portion 254 as best seen in FIG. 24.

The sample well tray further includes a plurality of aerosol discharge openings 260 located on the top surface 250 of the sample well tray, as shown in FIG. 24. In the example shown in FIG. 24, the sample well tray includes ninety-six of such aerosol discharge openings 260 arranged in a 8 by 12 array. As shown in FIG. 24, each aerosol discharge opening 260 corresponds to the four adjacent sample well openings 248.

Figure 25:
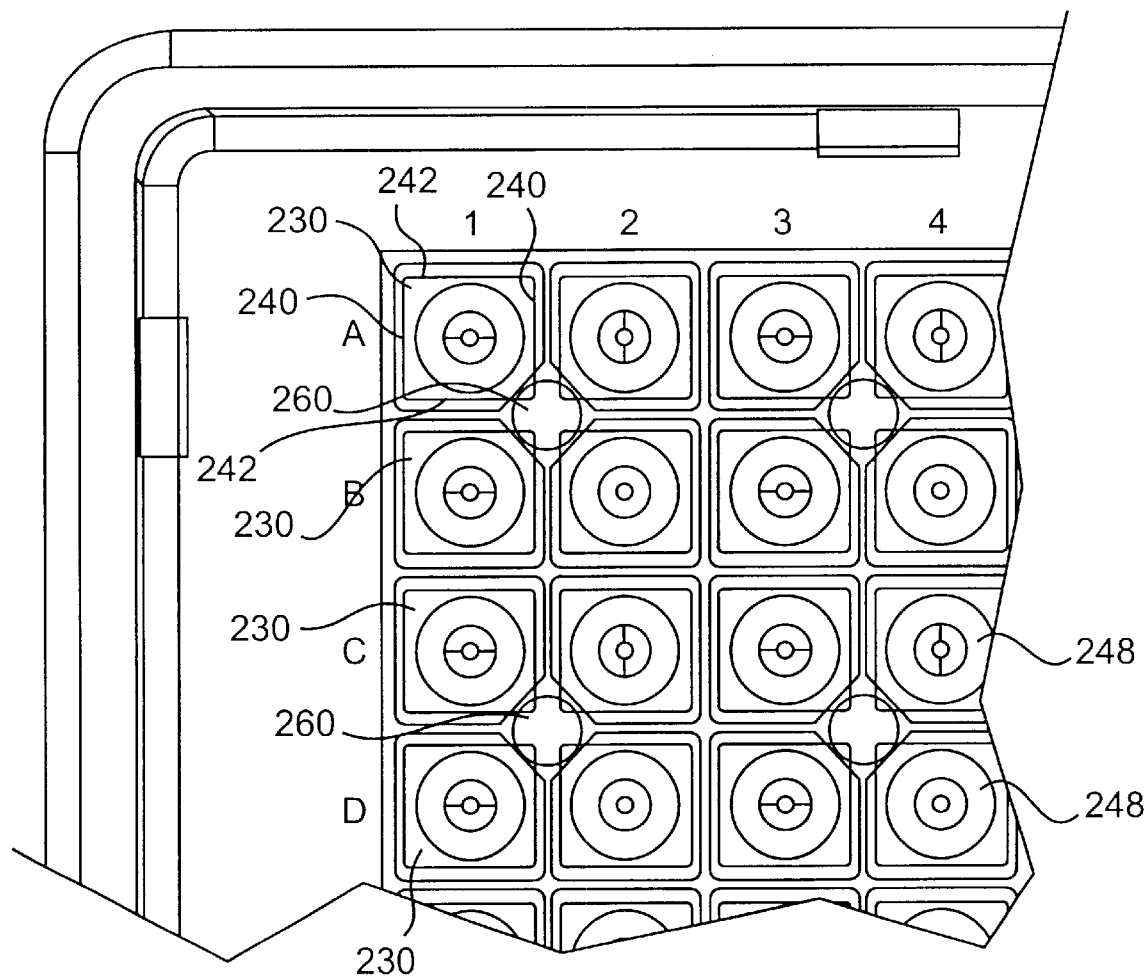

FIG. 25 schematically illustrates the positioning of the vent plate walls relative to the aerosol discharge openings. The aerosol discharge openings facilitate the flow of aerosols from the sample wells in a manner which will be described below. When the purification tray and vent plate are positioned on top of the sample well tray, each drip director is inserted inside of the top portion of a corresponding sample well opening 248. The bottom surface of each vent wall 240 and 242 preferably abuts the top surface 250 of the sample well tray. If no aerosol discharge openings were provided, the aerosols would have difficulty escaping the sample wells. However, it is undesirable to allow large amounts of aerosols to build up in the sample wells. Therefore, in the embodiment of FIGS. 21–25, an aerosol discharge aperture 260 is provided to assist in allowing the aerosols from the four adjacent sample wells to escape.

As shown in FIG. 25, the aerosol discharge apertures 260 and vent plate walls 240 and 242 are configured so that the aerosol discharge aperture 260 overlaps with the four adjacent vent chambers 230. For example, an aerosol discharge aperture 260 is provided in between sample wells C1, C2, D1, and D2. The aerosol discharge aperture 260 is sized so that each of the rectangular vent chambers 230 (defined by perpendicularly intersecting vent walls 240 and 242) overlaps with the aerosol discharge aperture 260 so that aerosols formed in each of the vent chambers may be drawn out of the vent chambers and downward through the aerosol discharge aperture 260. This configuration creates a flow path from each sample well so that the aerosols are directed toward the aerosol discharge aperture and away from the sample wells. The second embodiment also includes a vacuum chamber for imposing a pressure differential between the top and bottom of the purification tray. In this embodiment, the aerosols from a set of four adjacent sample wells flow through a common aerosol discharge opening. The aerosols from the set of sample well will not enter the adjacent sample wells because they are constantly urged toward the aerosol discharge aperture by the pressure differential created by the lower vacuum chamber. In this manner, cross-contamination between different sample wells is minimized.

The sample well tray 208 shown in FIG. 24 further includes alignment notches 262 which may be utilized for aligning a gap pad (not shown) on the sample well tray. The sample well tray of the second embodiment may be made out of any suitable material and by any suitable method such as injection molding.

Figure 26A:
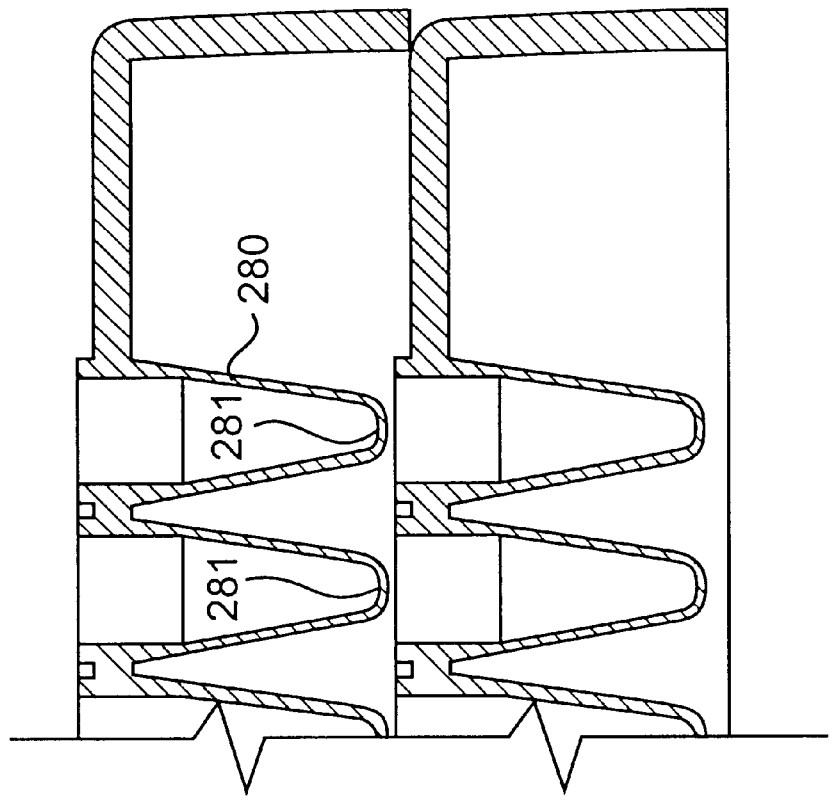

The sample well trays according to the second embodiment of the invention may include a preferred geometry which is particularly well-suited for stacking. FIG. 26A illustrates the geometry of a current sample well tray 270. As shown in FIG. 26A, the bottom portion 273 of the sample wells 272 of the top sample well tray 270 project into the openings 274 of the sample wells located below it when the trays are stacked. This geometry helps to reduce the shipping volume of the sample well trays when they are shipped. However, because the sample well bottom portion 273 of the top tray projects into the opening in bottom sample well tray, the top sample well 270 may abut against the inner surface of the bottom sample well if the top sample well tray moves horizontally relative to the bottom sample well tray. This lateral movement may cause bending and permanent damage to the sample wells. In addition, the arrangement may cause damage to adhesive and heat sealed covers if the trays are stacked for storage, incubation, or placed in a stacker or elevator for robotic handling.

Figure 26B:
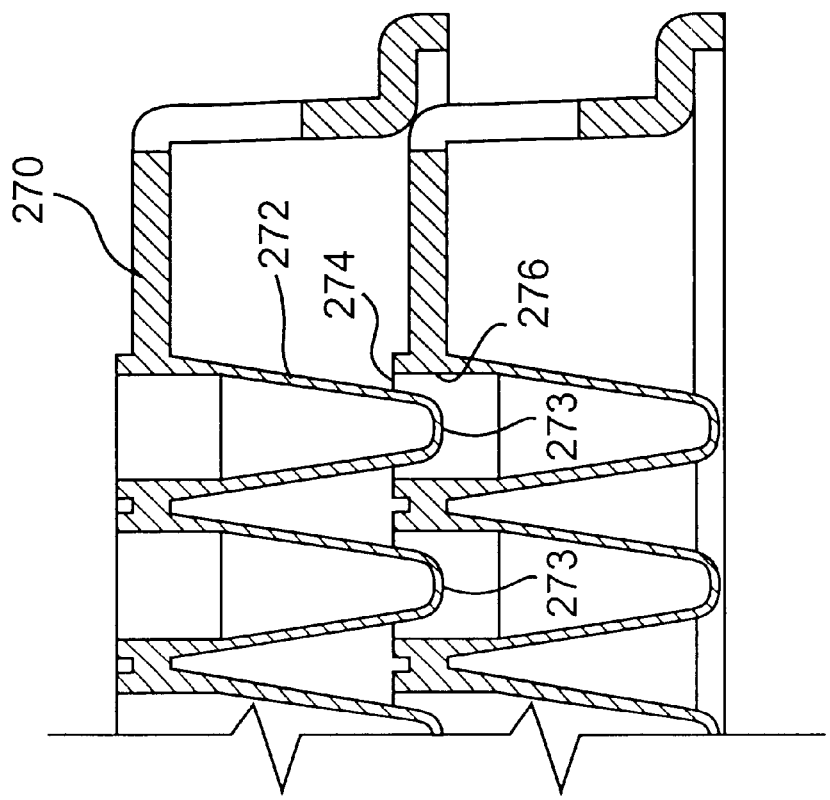
Figure 27:
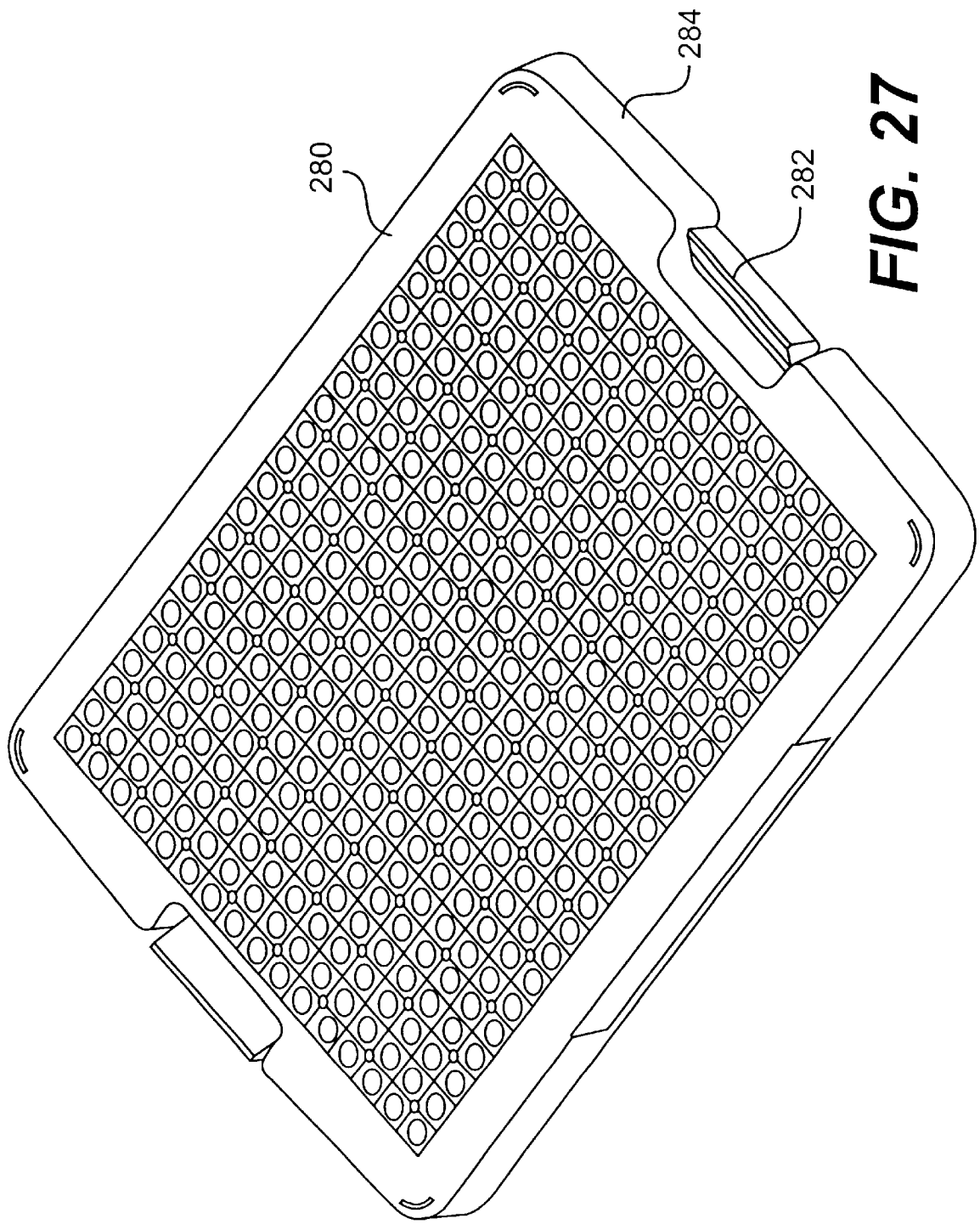
Figure 28A:
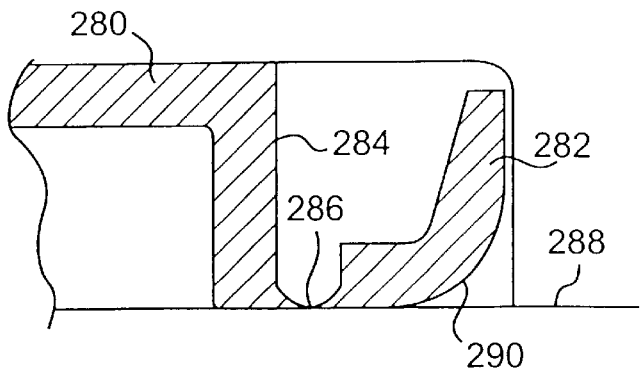
Figure 28B:
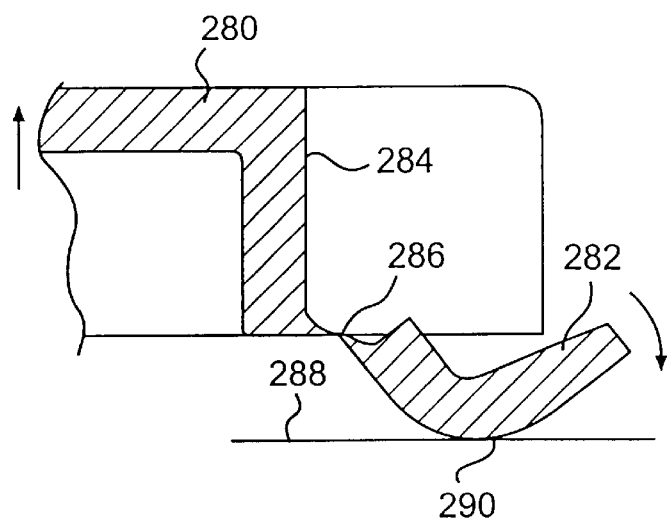

FIG. 26B illustrates a sample well tray geometry according to the present invention that helps to obviate these problems. As shown in FIG. 26B, the bottom portions 281 of the sample wells 280 of the top sample well tray do not project into the sample wells of the bottom sample well tray. Therefore, relative movement in the horizontal direction between the top and bottom sample well tray will not cause damage to the sample wells.

FIGS. 27–30 illustrate two alternative examples of sample well trays that are suitable for use with the purification apparatus instead of the FIG. 24 sample well tray. The sample well trays shown in FIGS. 27-30 include a removal mechanism as part of the sample well tray. In the past, a separate removal tool was typically used in order to remove the sample well trays from a sample block. The present invention eliminates the need for a separate removal tool by incorporating a removal mechanism into the sample well tray. As embodied herein and shown in FIGS. 27–28, the sample well tray 280 may include a hinged cam 282 for assisting in the removal of the sample well tray from the device. In the example shown, the hinged cam 282 is connected to the side 284 of sample well tray 280 by a small connecting piece 286. FIG. 28A shows the hinged cam 282 in a disengaged position so that the bottom of the sample well tray 280 is resting on surface 288. When it is desired to remove the sample well tray 280 from the apparatus, the hinged cam 282 may be grasped manually or by a tool, and rotated downward. As shown in FIG. 28B, when the hinged cam is rotated about the connecting piece 286, the sample well tray is lifted upwards as a result of the cam portion 290 of the hinged cam contacting the surface 288. This removal mechanism thereby easily lifts up the sample well tray without the need for a separate removal tool.

Figure 30A:
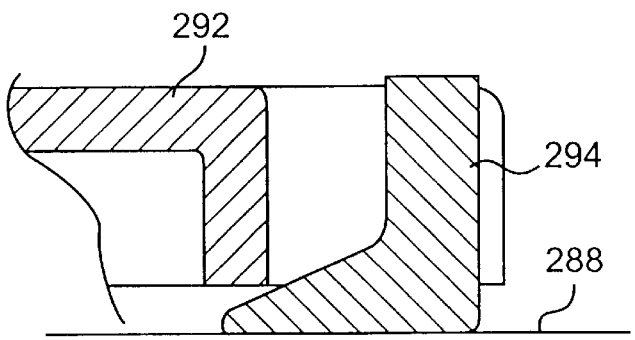
Figure 30B:
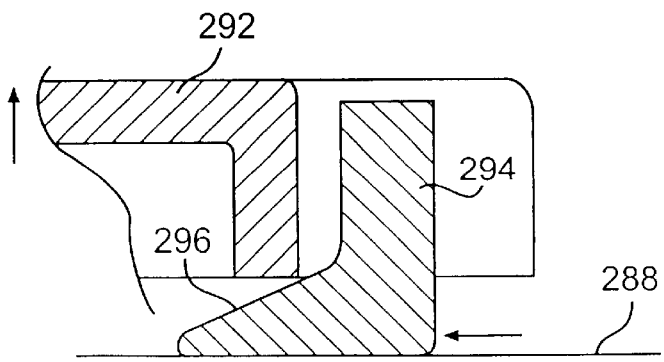
Figure 29:
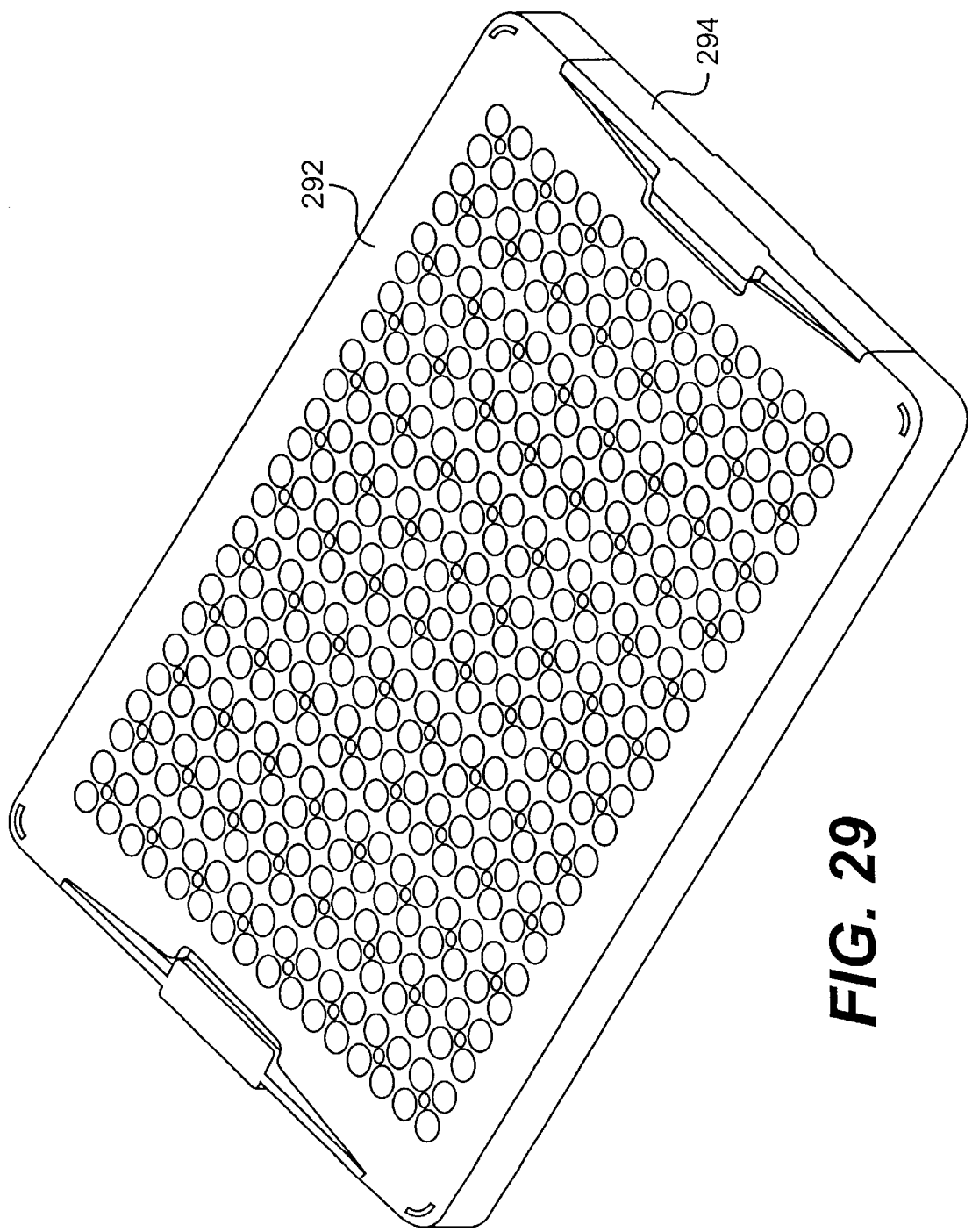

FIGS. 29–30 illustrate another example of a sample well tray having a removal mechanism. As shown in FIGS. 29–30, the sample well tray 292 includes a sample well tray removal mechanism in the form of a wedge 294. In the first position shown in FIG. 30A, the sample well tray 292 is spaced from the wedge 294. However, the wedge may be gripped manually and pushed inward so that the ramp surface 296 engages the bottom edge 298 of the sample well tray and pushes the sample well tray upward.

It will be apparent to those skilled in the art that various modifications and variations can be made in the purification apparatus and method for processing a plurality of fluid samples, use of the apparatus of the present invention, and in construction of this apparatus, without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A filtration apparatus for processing a plurality of fluid samples, comprising:
   a purification tray, said purification tray comprising:
      a filter plate having a plurality of columns with discharge openings at the bottom thereof,
      a plurality of filters aligning with the columns of the filter plate, and
      a vent plate including flow obstructions; and
   a sample well tray having a plurality of sample wells aligned with the columns of the filter plate for receiving fluid from the discharge openings,
   wherein the vent plate is positioned in a space between the filter plate and the sample well tray, the vent plate flow obstructions positioned adjacent said sample wells for limiting cross-contamination between sample wells, the flow obstructions defining at least one discrete flow path for permitting aerosols from a sample well to pass therethrough out of the respective sample well.

2. The filtration apparatus of claim 1, wherein said flow obstructions of the vent plate comprise an aerosol discharge element on the vent plate corresponding to a sample well, said aerosol discharge element substantially surrounding an opening of the corresponding sample well of the adjacent sample well tray, the at least one discrete flow path of the flow obstructions of the vent plate allowing aerosols to pass through the aerosol discharge element to reduce the amount of aerosols in the sample wells.

3. The filtration apparatus of claim 2, wherein the sample well tray comprises at least one aperture extending through the sample well tray from a top surface adjacent the vent plate to a bottom surface thereof so that the aerosols that pass through the flow obstruction discrete flow path may be evacuated from the space between the vent plate and the sample well tray.

4. The filtration apparatus of claim 3, wherein said discrete flow paths in the obstructions of the vent plate are substantially aligned with a corresponding said aperture extending through the sample well tray.

5. The filtration apparatus of claim 2, wherein the aerosol discharge element comprises a generally cylindrical projection extending from the vent plate, and said discrete flow paths are defined by at least one notch in the cylindrical projection.

6. The filtration apparatus of claim 5, further comprising a plurality of apertures in the sample well tray, the plurality of apertures extending through the sample well tray from a top surface adjacent the vent plate to a bottom surface thereof, and wherein the plurality of apertures are substantially aligned with an adjacent corresponding notch in the cylindrical projection.

7. The filtration apparatus of claim 6, wherein the cylindrical projection inhibits aerosols from one sample well from flowing into an adjacent sample well, and a substantial portion of the aerosols flowing through the corresponding notch in the vent plate exit out of the corresponding aligned aperture.

8. The filtration apparatus of claim 5, further comprising at least one raised cylindrical surface on a top surface of the sample well tray, said raised cylindrical surface having a diameter approximately corresponding to the diameter of the cylindrical projection of the aerosol discharge element of the vent plate so that the raised cylindrical surface and cylindrical projection may generally abut against one another when the purification tray is positioned on the sample well tray.

9. The filtration apparatus of claim 3, wherein the flow obstructions in the vent plate comprise a plurality of perpendicularly extending walls forming an aerosol flow chamber, and wherein the sample well tray includes a plurality of apertures, the plurality of apertures extending through the sample well tray from a top surface adjacent the vent plate to a bottom surface thereof.

10. The filtration apparatus of claim 9, wherein a single aperture in the sample well tray is configured to communicate with four of said aerosol flow chambers of the vent plate so that aerosols may exit the four aerosol flow chambers and pass through the aperture.

11. The filtration apparatus of claim 9, wherein four aerosol flow chambers are provided for the aperture in the sample well tray.

12. The filtration apparatus of claim 1, wherein said vent plate is composed of a non-porous material.

13. The filtration apparatus of claim 12, wherein said non-porous material is a polymer.

14. The filtration apparatus of claim 1, wherein the purification tray further comprises a heat transfer plate positioned between at least a portion of the filter plate and at least a portion of the vent plate, said heat transfer plate including a plurality of openings corresponding to individual columns of the filter plate, wherein the heat transfer plate is configured to transfer heat to the filter plate.

15. The filtration apparatus of claim 14, wherein the heat transfer plate is attached adjacent the filter plate, and the vent plate is attached adjacent the heat transfer plate.

16. The filtration apparatus of claim 1, wherein said columns of the filter plate are of substantially unitary construction.

17. The filtration apparatus of claim 1, wherein said filters are capable of filtering nucleic acids.

18. The filtration apparatus of claim 14, further comprising a frame for the purification tray, said frame including a heater assembly for providing heat to the heat transfer plate.

19. The filtration apparatus of claim 18, wherein the heater assembly comprises a contact heater for engaging with said heat transfer plate when the purification tray is placed in said frame.

20. The filtration apparatus of claim 19, wherein said heat transfer plate further comprises side walls around the outer periphery of the filter plate columns, said contact heater contacting outer surfaces of the heat transfer plate sidewalls.

21. The filtration apparatus of claim 20, wherein said contact heater is biased toward the heat transfer plate.

22. The filtration apparatus of claim 18, wherein the heater assembly further comprises at least one temperature sensor for sensing the temperature of the purification tray.

23. The filtration apparatus of claim 22, wherein the temperature sensor is inserted into a column of the purification tray.

24. The filtration apparatus of claim 14, wherein said heat transfer plate includes a heat source.

25. The filtration apparatus of claim 18, wherein the frame defines a vacuum chamber below the purification tray in order to create a pressure differential to urge aerosols from inside the sample wells to flow along the discrete flow paths.

26. The filtration apparatus of claim 1, wherein the sample well tray includes a removal mechanism for assisting in the removal of the sample well tray from a block.

27. The filtration apparatus of claim 26, wherein the removal mechanism comprises a hinged cam member positioned on the outer periphery of the sample well tray, said hinged cam member lifting the sample well tray upward when the hinged cam member is pressed downward.

28. The filtration apparatus of claim 26, wherein the removal mechanism comprises a wedge outer member, the wedge outer member engaging with a bottom surface of the sample well tray to lift the sample well tray upward when the wedge outer member is pressed inward.

29. A purification tray for processing a plurality of fluid samples into sample wells, comprising:
   a filter plate having a plurality of columns with discharge openings at the bottom thereof;
   at least one filter positioned in the columns of the filter plate for filtering the fluid samples as they pass therethrough;
   a vent plate positioned between said filter plate and said sample wells, said vent plate including vents for permitting aerosols from the sample wells to escape; and
   a heat transfer plate positioned between the vent plate and a portion of the filter plate, said heat transfer plate configured to transfer heat to the columns of the filter plate.

30. The purification tray of claim 29, wherein said heat transfer plate includes apertures for receiving therethrough a plurality of columns of the filter plate.

31. The purification tray of claim 30, wherein said apertures in the heat transfer plate abut outside surfaces of the plurality of columns to retain the columns substantially at their spacing during heating.

32. The purification tray of claim 30, wherein said heat transfer plate includes side walls extending along the outside periphery of the filter plate columns, said side walls configured for contacting a heat source.

33. The purification tray of claim 32, wherein said side walls of the heat transfer plate extend perpendicular to a flat portion of the heat transfer plate containing said apertures, said side walls extending substantially parallel to the columns.

34. The purification tray of claim 33, wherein said heat source for the heat transfer plate comprises a frame surrounding the periphery of the heat transfer plate, said heat source further comprising a plurality of heaters positioned in the frame for contacting the side walls of the heat transfer plate when the heat transfer plate is positioned within the frame.

35. The purification tray of claim 34, wherein the plurality of heaters include a contact heater, said heat source further including a spring device for biasing the contact heater against a side portion of the heat transfer plate to provide contact between said contact heater and the side portion of the heat transfer plate.

36. The purification tray of claim 34, wherein the heat source further includes a temperature sensor for sensing the temperature inside the frame.

37. The purification tray of claim 30, wherein each said column of the filter plate comprises a first tapered cylindrical portion joined to a second tapered cylindrical portion having the discharge opening, said first tapered cylindrical portion having a diameter greater than the second tapered cylindrical portion, wherein the heat transfer plate contacts the columns in the region adjacent where the first tapered cylindrical portion joins the second tapered cylindrical portion.

38. The purification tray of claim 37, wherein the filters are located in the columns so that the filters rests against ribs provided adjacent the area of the column where the first tapered cylindrical portion joins the second tapered cylindrical portion.

39. The purification tray of claim 38, wherein the filters are located in the first tapered cylindrical portion of the columns.

40. The purification tray of claim 39, wherein said heat transfer plate includes a heater mounted on the heat transfer plate.

41. The purification tray of claim 29, wherein said vent plate is composed of non-porous material.

* * * * *